(12) United States Patent
Negishi et al.

(10) Patent No.: US 7,919,198 B2
(45) Date of Patent: Apr. 5, 2011

(54) CONDENSED RING AROMATIC COMPOUND FOR ORGANIC LIGHT-EMITTING DEVICE AND ORGANIC LIGHT-EMITTING DEVICE HAVING THE SAME

(75) Inventors: Chika Negishi, Yokosuka (JP); Akihito Saitoh, Yokohama (JP); Hiroki Ohrui, Kawasaki (JP); Hironobu Iwawaki, Yokohama (JP); Masanori Muratsubaki, Hachioji (JP)

(73) Assignee: Canon Kabushiki Kaisha, Tokyo (JP)

( * ) Notice: Subject to any disclaimer, the term of this patent is extended or adjusted under 35 U.S.C. 154(b) by 205 days.

(21) Appl. No.: 12/443,102

(22) PCT Filed: Mar. 27, 2008

(86) PCT No.: PCT/JP2008/056632
§ 371 (c)(1),
(2), (4) Date: Mar. 26, 2009

(87) PCT Pub. No.: WO2008/120808
PCT Pub. Date: Oct. 19, 2008

(65) Prior Publication Data
US 2010/0026171 A1 Feb. 4, 2010

(30) Foreign Application Priority Data

Apr. 2, 2007 (JP) ................... 2007-096343
Feb. 20, 2008 (JP) ................... 2008-038299

(51) Int. Cl.
*H01L 51/54* (2006.01)
*H01J 1/63* (2006.01)
*C07C 211/54* (2006.01)
*C07C 25/13* (2006.01)
*C07C 25/18* (2006.01)
*C07D 401/10* (2006.01)
*C07D 401/14* (2006.01)

(52) U.S. Cl. ........ 428/690; 428/917; 313/504; 313/506; 570/129; 570/183; 546/255; 546/256; 564/426

(58) Field of Classification Search .................. None
See application file for complete search history.

(56) References Cited

U.S. PATENT DOCUMENTS

| | | | |
|---|---|---|---|
| 2004/0076853 A1 | 4/2004 | Jarikov | 428/690 |
| 2006/0210830 A1 | 9/2006 | Funahashi et al. | 428/690 |
| 2008/0286611 A1 | 11/2008 | Muratsubaki et al. | 428/704 |
| 2009/0102371 A1 | 4/2009 | Hashimoto et al. | 313/504 |
| 2009/0184630 A1 | 7/2009 | Negishi et al. | 313/504 |

FOREIGN PATENT DOCUMENTS

| | | |
|---|---|---|
| JP | 09-241629 | 9/1997 |
| JP | 10-189247 | 7/1998 |
| JP | 10-189248 | 7/1998 |
| JP | 10-294177 | 11/1998 |
| JP | 2001-102173 | 4/2001 |
| JP | 2003-238516 | 8/2003 |
| JP | 2006-256979 | 9/2006 |

OTHER PUBLICATIONS

Kung K. Wang et al., "Thermolysis of Benzoenyne—Allenes To Form Biradicals and Subsequent Intramolecular Trapping with a Teraarylallene To Generate Two Triarylmethyl Radical Centers," J. Org. Chem., vol. 64, No. 5, 1999, pp. 1650-1656. International Preliminary Report on Patentability mailed Oct. 15, 2009—6 pages.

*Primary Examiner* — Dawn L Garrett
(74) *Attorney, Agent, or Firm* — Fitzpatrick, Cella, Harper & Scinto

(57) ABSTRACT

Provided are a condensed ring aromatic compound for an organic light-emitting device, and an organic light-emitting device having optical output with high efficiency and high luminescence and having durability. An organic light-emitting device including an anode and a cathode, and a layer made of an organic compound interposed between the anode and the cathode, wherein at least one layer of the layers made of the organic compound contains a condensed ring aromatic compound shown in the following general formula [1]:

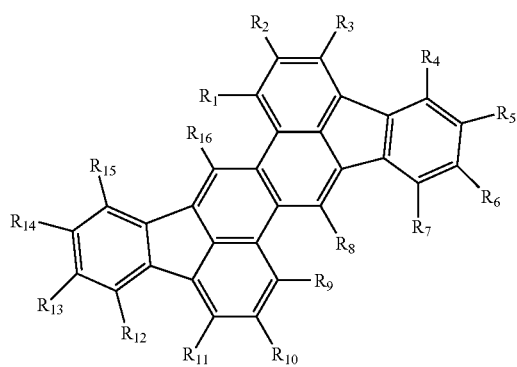

[1]

wherein $R_1$ to $R_{16}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and may be the same or different.

3 Claims, 6 Drawing Sheets

CONDENSED RING AROMATIC COMPOUND FOR ORGANIC LIGHT-EMITTING DEVICE AND ORGANIC LIGHT-EMITTING DEVICE HAVING THE SAME

TECHNICAL FIELD

The present invention relates to a condensed ring aromatic compound for an organic light-emitting device and an organic light-emitting device having the condensed ring aromatic compound.

BACKGROUND ART

An organic light-emitting device is a device having a thin film containing a fluorescent organic compound interposed between an anode and a cathode. Charging electrons and holes (right holes) from each of the electrodes allows to produce exciton of the fluorescent compound, thereby when this exciton returns to a base condition, the organic light-emitting device emits light.

Recent progress in organic light-emitting devices is remarkable, and examples of its characteristics include high luminance at a low applied voltage, variability of a light-emitting wavelength, high-speed responsibility, and capability of forming a thin and light-weighted light-emitting device. According to these characteristics, such a possibility has been suggested that organic light-emitting devices are used in a wide range of applications.

In the current status, however, light-emitting ability at further high luminance or high conversion efficiency are required. In addition, there are still many problems in view of durability such as deterioration due to change in time by use for a long period of time, or an atmospheric gas containing oxygen, and dampness.

Light emission such as blue, green and red with excellent color purity is necessary when considering application to a full-color display, and the like, but these problems also can not be recognized to be fully solved. Accordingly, a material for realizing an organic light-emitting device with good color purity, high light-emitting efficiency, and satisfactory durability has been required.

As a method for solving the above described problems, using a condensed ring aromatic compound for a constitutional material of an organic light-emitting device has been suggested. Japanese Patent Application Laid-Open No. 2001-102173, US Patent Application Laid-Open No. 2004-0076853, Japanese Patent Application Laid-Open No. 2006-256979, Japanese Patent Application Laid-Open No. H10-189248, and Japanese Patent Application Laid-Open No. H09-241629 are disclosed as examples of using a condensed ring aromatic compound for a constitutional material of an organic light-emitting device. However, the condensed ring aromatic compound of the present invention or the organic light-emitting device containing the compound as a constitutional material are not disclosed. Furthermore, J. Org. Chem. 64, 1650-1656, 1999 also discloses a condensed ring aromatic compound.

DISCLOSURE OF THE INVENTION

The present invention was made in order to solve the above described problems in the conventional techniques. That is, an object of the present invention is to provide a condensed ring aromatic compound for an organic light-emitting device. Another object of the present invention is to provide an organic light-emitting device having optical output with high efficiency and high luminance, and having durability.

The inventors of the present invention were studied in order to solve the above described problems, as a result, they achieved completion of the present invention. That is, a condensed ring aromatic compound for an organic light-emitting device represented by the following general formula [1] is provided according to the present invention.

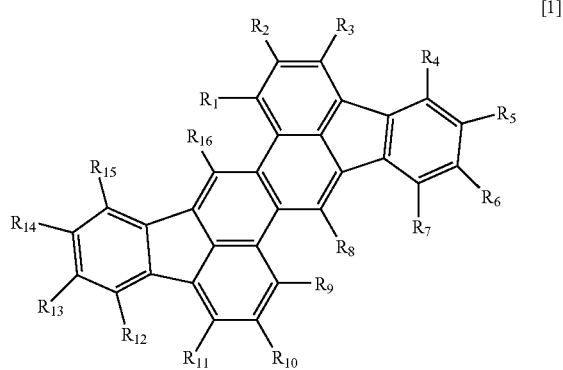

[1]

In the formula, $R_1$ to $R_{16}$ are independently represented by a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and they may be the same or different.

The condensed ring aromatic compound of the present invention has high quantum efficiency, and therefore, according to the present invention, an organic light-emitting device having optical output with high efficiency and high luminance, and having durability can be provided.

BEST MODE FOR CARRYING OUT THE INVENTION

Figure 1:
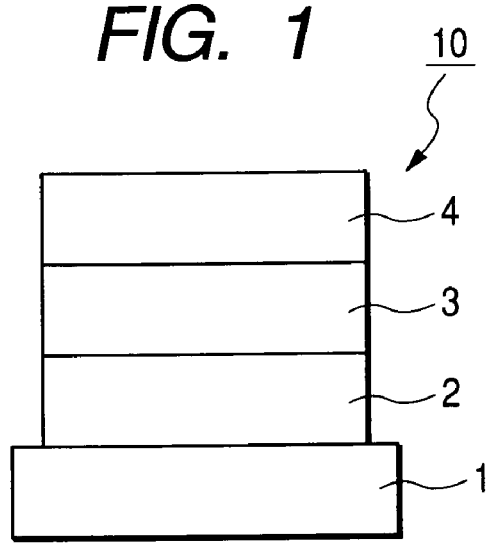
FIG. 1 is a cross-sectional view illustrating a first embodiment of the organic light-emitting device of the present invention.

The condensed ring aromatic compound of the present invention will be first described in detail. The condensed ring aromatic compound for an organic light-emitting device of the present invention is represented by the following general formula [1]: 2)

[1]

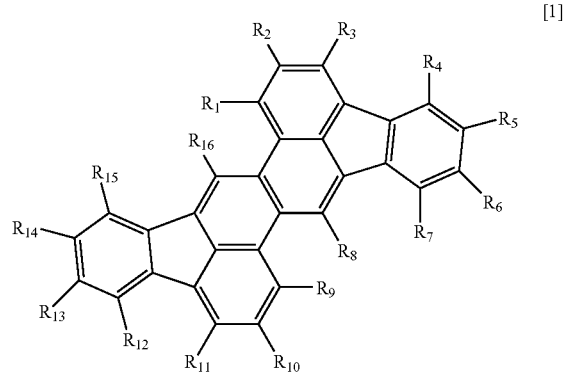

In the formula [1], $R_1$ to $R_{16}$ are independently represented by a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and they may be the same or different.

Specific examples of a substituent represented by $R_1$ to $R_{16}$ in the above general formula [1] are shown in the following. However, examples are not limited thereto.

Example of a halogen atom represented by $R_1$ to $R_{16}$ include fluorine, chlorine, bromine, and iodine.

Examples of an alkyl group represented by $R_1$ to $R_{16}$ include a methyl group, ethyl group, normal propyl group, isopropyl group, normal butyl group, tert-butyl group, sec-butyl group, normal pentyl group, octyl group, 1-adamantyl group, 2-adamantyl group, benzyl group, and phenethyl group.

Examples of an alkoxy group represented by $R_1$ to $R_{16}$ include a methoxy group, ethoxy group, propoxy group, 2-ethyl-octyloxy group, and benzyloxy group.

Examples of an aryloxy group represented by $R_1$ to $R_{16}$ include a phenoxy group, 4-tert-butylphenoxy group, and thienyloxy group.

Examples of an amino group represented by $R_1$ to $R_{16}$ include an N-methylamino group, N-ethylamino group, N,N-dimethylamino group, N,N-diethylamino group, N-methyl-N-ethylamino group, N-benzylamino group, N-mehtyl-N-benzylamino group, N,N-dibenzylamino group, anilino group, N,N-diphenylamino group, N,N-dinaphthylamino group, N,N-difluorenylamino group, N-phenyl-N-tolylamino group, N,N-ditolylamino group, N-metyl-N-phenylamino group, N,N-dianisorylamino group, N-mesityl-N-phenylamino group, N,N-dimesitylamino group, N-phenyl-N-(4-tert-butylphenyl)amino group, N-phenyl-N-(4-trifluoromethylphenyl)amino group, N,N-di(4-tert-butylphenyl)amino group, N,N-di(3,5-dimethylphenyl)amino group, N-(9,9-dimethyl-fluorenyl)-N-phenylamino group, N-(9,9-dimethyl-fluorenyl)-N-tolylamino group, N-(9,9-dimethyl-fluorenyl)-N-(3,5-dimethylphenyl)amino group, and N-(9,9-dimethyl-fluorenyl)-N-(2-naphthyl)amino group.

Examples of an aryl group represented by $R_1$ to $R_{16}$ include a phenyl group, naphthyl group, pentalenyl group, indenyl group, azulenyl group, anthryl group, pyrenyl group, indacenyl group, acenaphthenyl group, phenanthryl group, phenalenyl group, fluorantenyl group, acephenanthryl group, aceanthryl group, triphenyrenyl group, chrysenyl group, naphthacenyl group, perirenyl group, pentacenyl group, biphenyl group, terphenyl group, and fluorenyl group.

Examples of an aryl group represented by $R_1$ to $R_{16}$ also include substituents derived from the following compound.

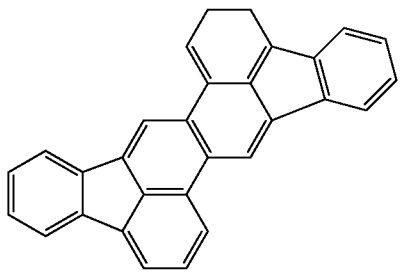

The compound mentioned above may be possessed halogen atom, alkyl group such as methyl group, ethyl group, isopropyl group, tert-butyl group, alkoxy group such as methoxy group, ethoxy group, propoxy group, aryloxy group such as phenoxy group, 4-tert-butylphenoxy group, amino group such as N,N-diphenylamino group, N,N-dinaphthylamino group, aryl group such as phenyl group, naphthyl group or heterocyclic group such as pyridyl group and pyrrolyl group.

Examples of a heterocyclic group represented by $R_1$ to $R_{16}$ include a pyridyl group, pyrrolyl group, oxazolyl group, oxasiazolyl group, thiazolyl group, thiadiazolyl group, quinolyl group, isoquinolyl group, carbazolyl group, acridinyl group, and phenanthrolyl group.

Examples of a substituent that may be contained in an alkyl group, an aryl group and a heterocyclic group represented by $R_1$ to $R_{16}$ include alkyl groups such as a methyl group, an ethyl group, and a propyl group, an aralkyl group such as a benzyl group, aryl groups such as a phenyl group and a biphenyl group, heterocyclic groups such as a pyridyl group and a pyrrolyl group, amino groups such as a dimethylamino group, diethylamino group, dibenzylamino group, diphenylamino group, ditolylamino group, and dianisolylamino group, alkoxy groups such as a methoxy group, an ethoxy group, and a propoxy group, an aryloxy group such as a phenoxyl group, halogen atoms such as fluorine, chlorine, bromine, and iodine, and a cyano group.

A condensed ring aromatic compound represented by the general formula [1] can be synthesized by, for example, a method showing in the following synthesis route 1 or 2 or 3. Synthesis Routes 1

The condensed ring aromatic compound represented by the general formula [1] can be synthesized using a dibromochrysene derivative and a 2-hydroxyphenylboronic acid derivative, or a bromochloroiodobenzene derivative as raw materials, for example, as shown in the following synthesis route 1, however, a synthesis method is not limited thereto.

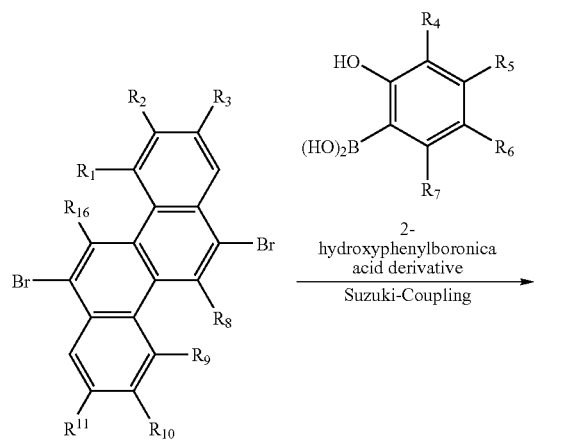

Dibromochrysene derivative

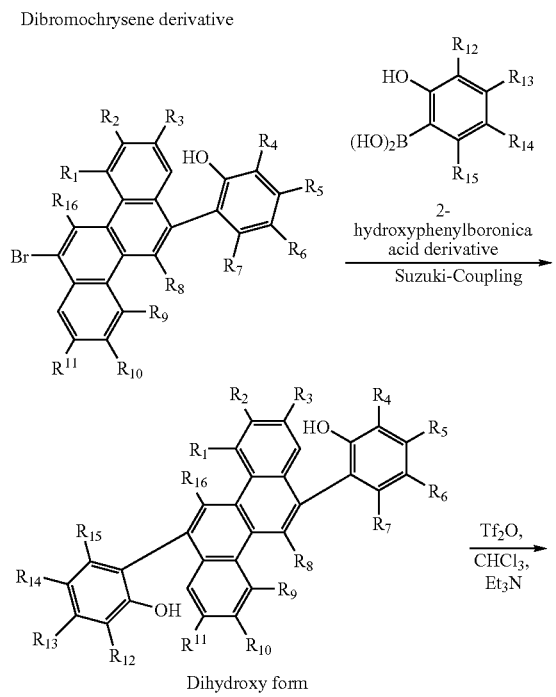

Dihydroxy form

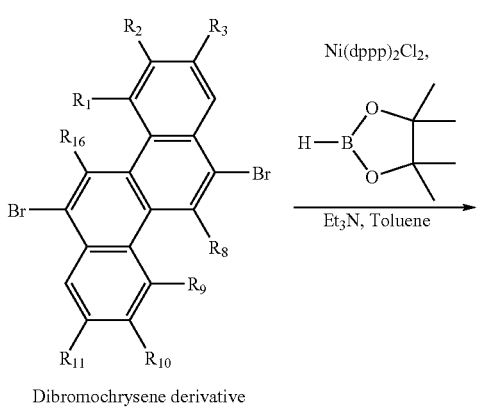

Dibromochrysene derivative

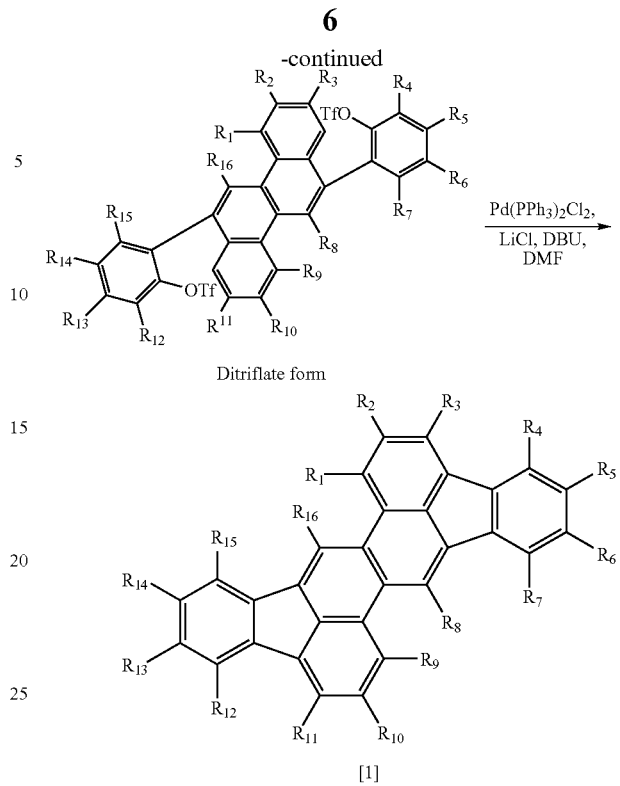

[1]

A specific method of the synthesis route 1 is described. First, a dihydroxy form is synthesized by a suzuki-miyaura coupling reaction of a dibromochrysene derivative with a 2-hydroxyphenylboronic acid derivative (for example, Chem. Rev. 1995, 95, 2457-2483). As another method, for instance, the Yamamoto method using a nickel catalyst (for example, Bull. Chem. Soc. Jpn. 51, 2091, 1978) is also exemplified. The synthesized dihydroxyl form is then induced to a ditriflate form, and intramolecular cyclization (for example, J. Org. Chem. 68, 883-887, 2003) is carried out on the ditriflate form. Thereby, a condensed ring aromatic compound represented by the general formula [1] can be obtained.

Synthesis Routes 2

The condensed ring aromatic compound represented by the general formula [1] can be synthesized using a dibromochrysene derivative and a bromochloroiodobenzene derivative as raw materials, for example, as shown in the following synthesis route 2.

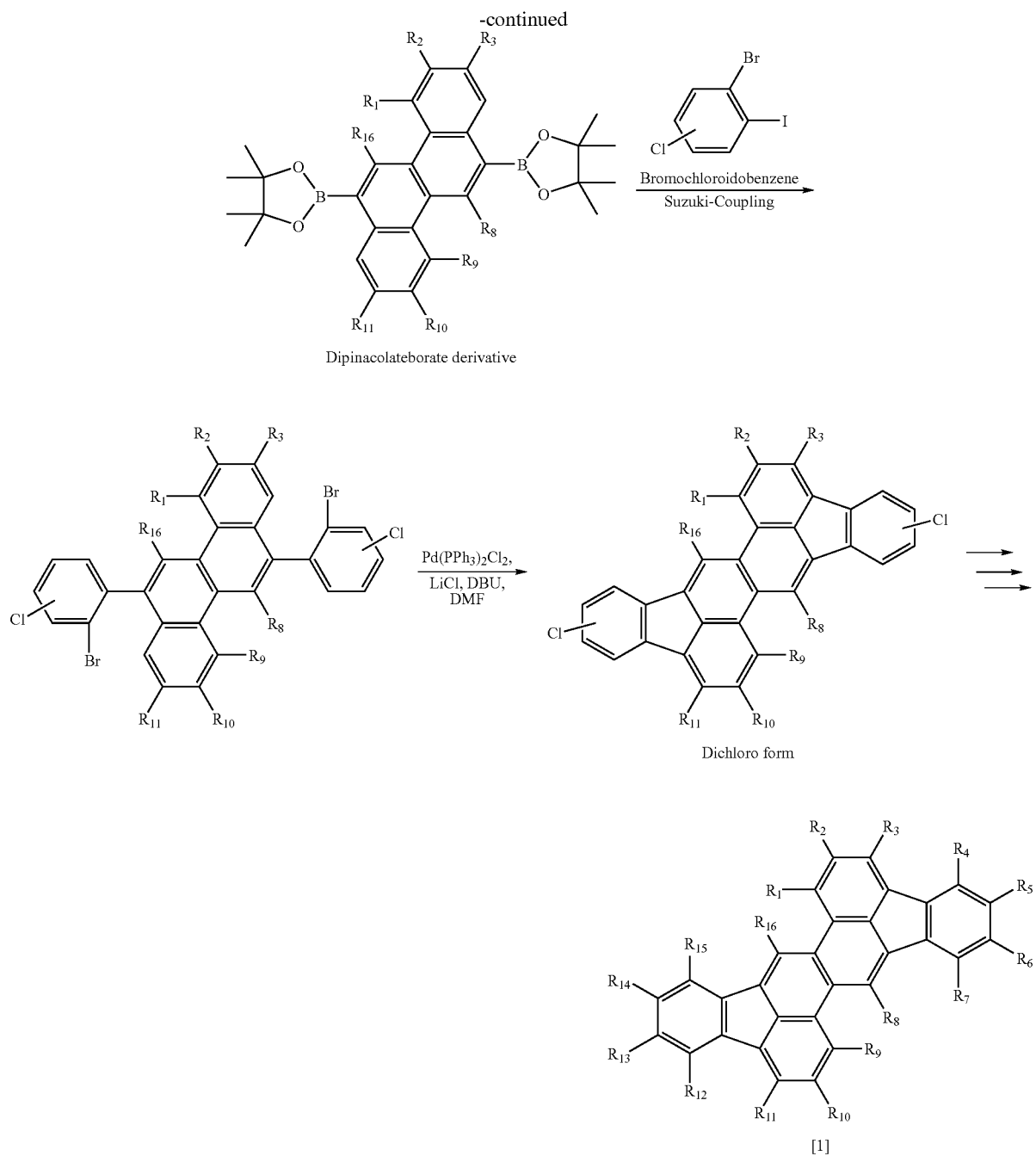

[1]

A specific method of the synthesis route 2 is described.

The synthesis route 2 is a synthesis method undergoing a dichloro form that is a produced compound of the third step in the above described synthesis steps. This route is particularly useful for the case of simply and easily introducing various substituents from $R_4$ to $R_7$ or from $R_{12}$ to $R_{15}$ in the general formula [1]. Specifically, a dibromochrysene derivative is induced to a dipinacolate form (for example, J. Org. Chem. 65, 164, 2000). Then, a suzuki-miyaura coupling reaction with a bromochloroiodobenzene derivative is carried out, and subsequently cyclization is carried out in the similar technique to the intramolecular cyclization reaction in the above described synthesis route 1 (for example, J. Org. Chem. 68, 883-887, 2003) thereby inducing to a dichloro form.

Examples of a synthesis method of introducing various substituents using this dichloro form, as an intermediate are described in the following.

For instance, the examples include coupling reactions such as suzuki-miyaura coupling reaction (J. Am. Chem. Soc. 120, 9722, 1998), Still reaction (Macromolecules. 18, 321, 1985), and Heck reaction (J. Org. Chem. 46, 1067, 1981).

Synthesis Route 3

A condensed ring aromatic compound represented by the general formula [1] can be also synthesized using a dibromochrysene derivative as a raw material, for example, as shown in the following synthesis route 3.

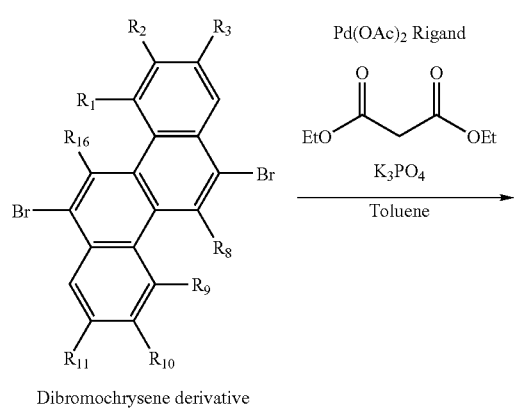
Dibromochrysene derivative
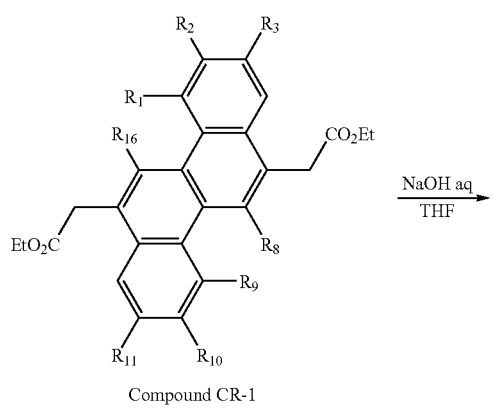
Compound CR-1
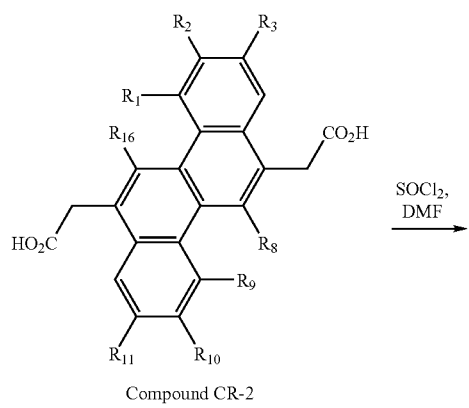
Compound CR-2
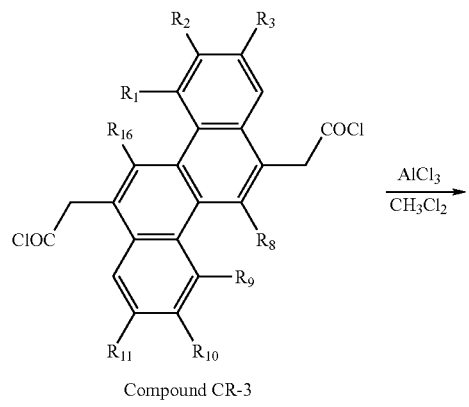
Compound CR-3
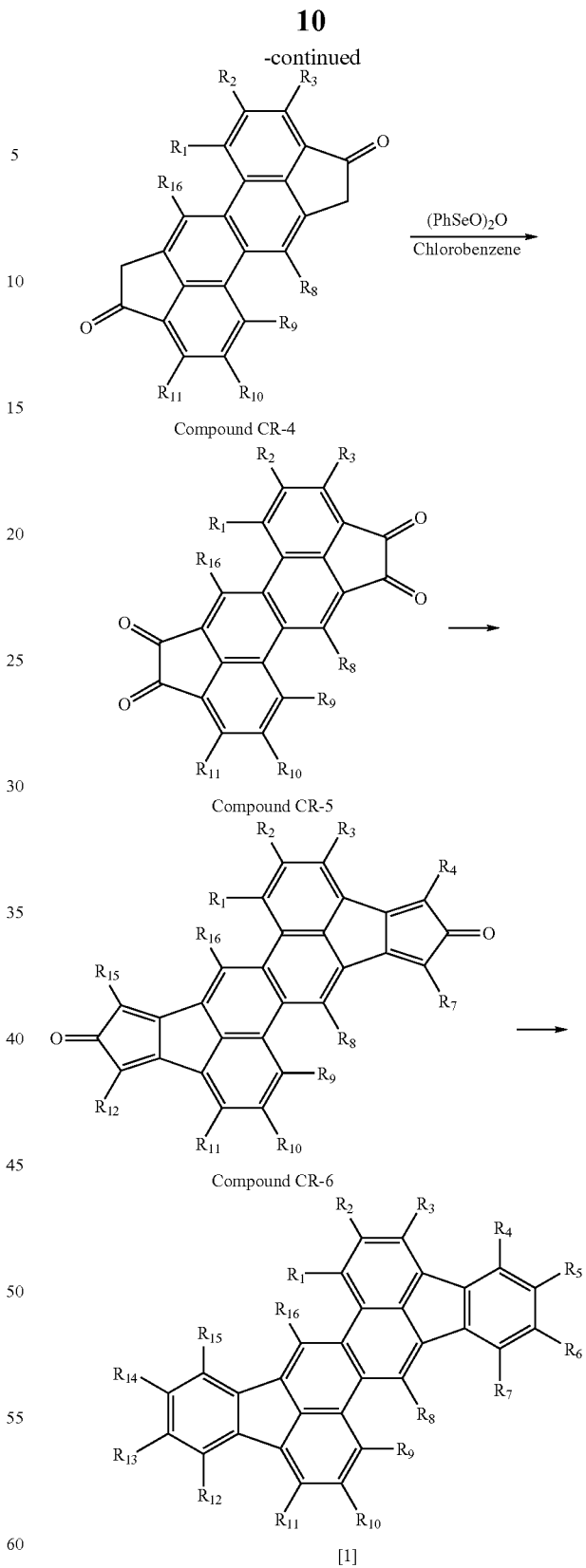
A specific method of the synthesis route 3 is described.
The synthesis route 3 is particularly useful for the case of simply and easily introducing various substituents from $R_4$ to $R_7$ or from $R_{12}$ to $R_{15}$ in the general formula [1]. Specifically, a dibromochrysene derivative is induced to a compound CR-1 that is an ester form. Then, hydrolysis is carried out on the ester form to induce to a compound CR-2, and undergoing a subsequent step, and then induced to a compound CR-3 that is an acid chloride. Furthermore, by subjecting to intramolecular cyclization (for example, J. Am. Chem. Soc. 105, 7375, 1983), the compound CR-3 is induced to a ketone form. This ketone form is conversed into a diketone form (for example, Bull. Chem. Soc. Jpn. 59, 3311, 1986). Using this diketone form as an intermediate, after undergoing the two steps of Knoevenagel reaction (for example, Eur. J. Org. Chem. 4185, 2002) and Diels-Alder reaction (for example, J. Org. Che. 62, 530, 1997), various substituents are introduced from $R_4$ to $R_7$ or from $R_{12}$ to $R_{15}$.

In order to enhance light-emitting efficiency of an organic light-emitting device, generally, it is desired that light-emitting quantum efficiency of a light-emitting center material itself is large.

A compound in which all of $R_1$ to $R_{16}$ are hydrogen atoms in the general formula [1] has high light-emitting quantum efficiency in a diluted solution as shown in Example 1. Therefore, when the compound of the general formula [1] is used as a material of an organic light-emitting device, it can be expected that the light-emitting efficiency of the device be increased.

Further, by introducing substituents into $R_1$ to $R_{16}$ in the general formula [1], decrease in the light emitting-efficiency due to molecule association can be reduced. Particularly, to introduce substituents into $R_1$, $R_4$, $R_7$, $R_8$, $R_9$, $R_{12}$, $R_{15}$, $R_{16}$ has large effect of reducing decrease in light-emitting efficiency caused by molecule association since the substituents are easily positioned in the perpendicular direction to the plane of the compound represented by the general formula [1] due to steric hindrance of adjacent substituents.

Examples of substituents giving steric hindrance to a molecule itself include an alkyl group, alkoxy group, aryloxy group, amino group, aryl group, and heterocyclic group. Preferable examples include an amino group, aryl group and heterocyclic group.

In addition, when the compound represented by the general formula [1] is used as a light-emitting layer, the compound can be used for any of a host material and a guest material. Particularly, when a compound represented by the general formula [1] as a host material in a light-emitting layer, the material preferably has a high glass transition temperature, and accordingly, the compound desirably has substituents at $R_1$ to $R_{16}$.

Examples of substituents for improving a glass transition temperature preferably include an amino group, an aryl group, and a heterocyclic group.

An example of a substituent to be introduced for using the compound represented by the general formula [1] as an intermediate in the synthesis step is a halogen atom. In this case, iodine, bromine and chlorine are preferable from the viewpoint of a degree of activity in a synthesis reaction.

A compound used as a material of an organic light-emitting device is desirably has high carrier injecting property. Promoting carrier injection allows the device to drive at a low voltage. Examples of a substituent to be introduced in order to have high carrier injecting property preferably are preferably an amino group and a heterocyclic group. Generally, when an amino group is introduced as a substituent, hole injecting property is improved. Whereas when a heterocyclic group is introduced, electron injecting property is improved.

An unsubstituted form of the condensed ring aromatic compound of the present invention shows blue color with preferably color purity in the case of converting a light-emitting wavelength in a diluted solvent to CIE chromaticity coordinate. Therefore, introducing a substituent extending π conjugate into this unsubstituted form enables to transform to a light emitting color in the long wavelength side from blue colors. Examples of a substituent for extending π conjugate include an amino group, an aryl group and a heterocyclic group.

Specific examples of the compound in the above-described general formula [1] are shown in the following. However, the present invention is not limited to these examples.

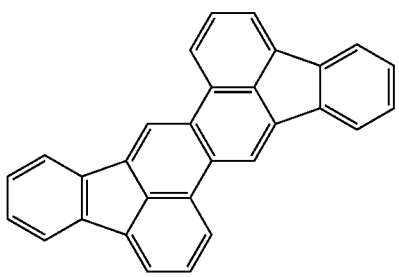

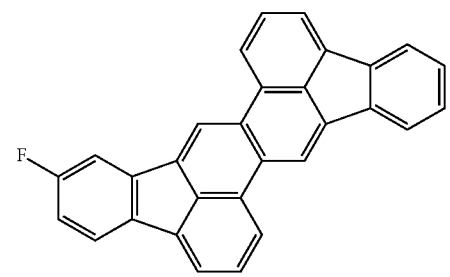

B-1

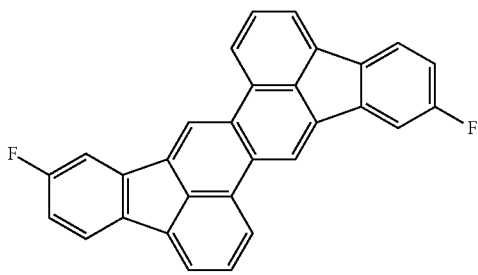

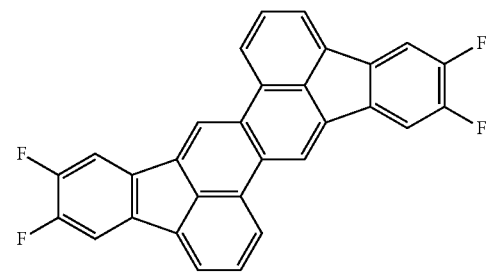

B-3

-continued
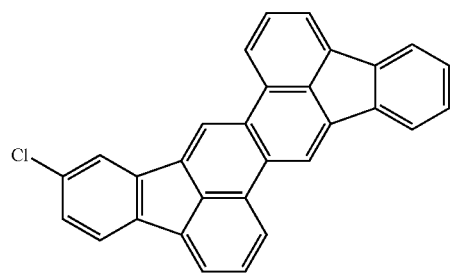
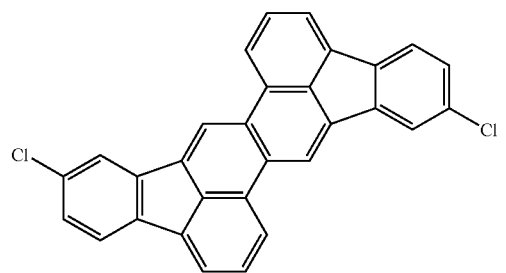
B-5
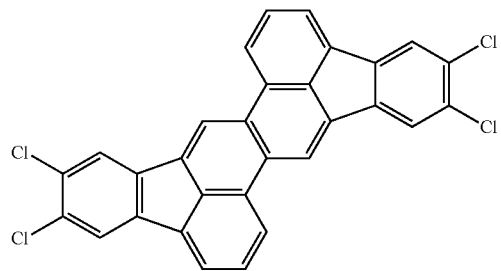
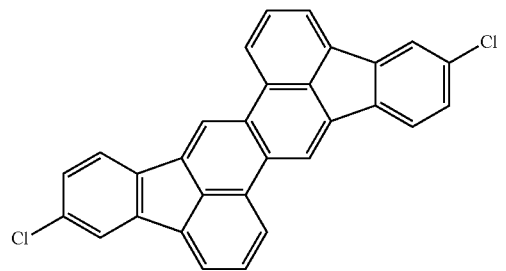
B-7
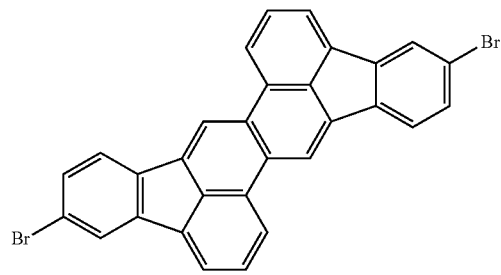
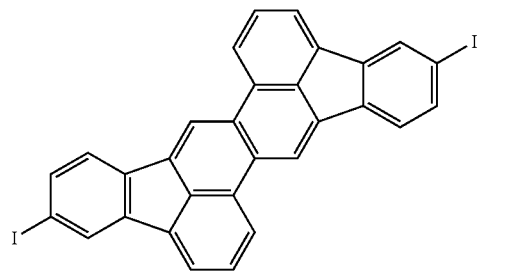
B-9
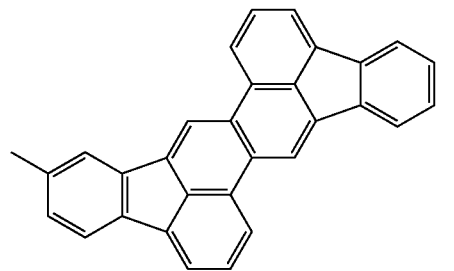
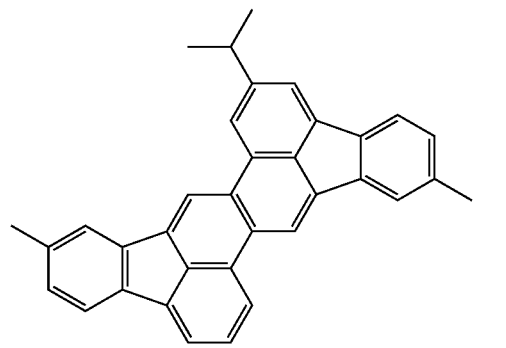
C-1
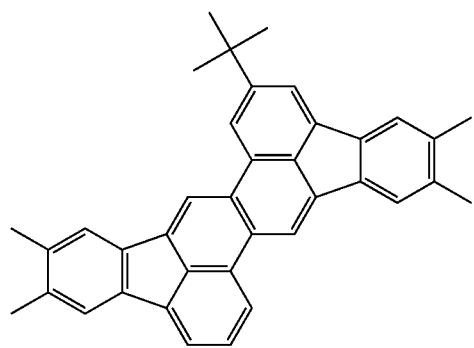
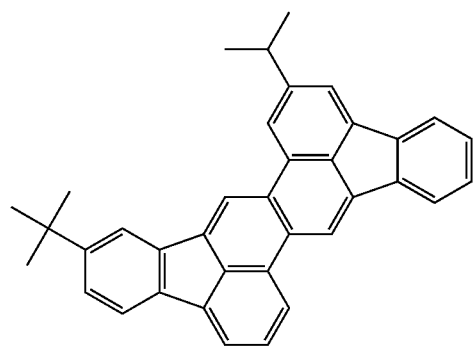
C-4

-continued
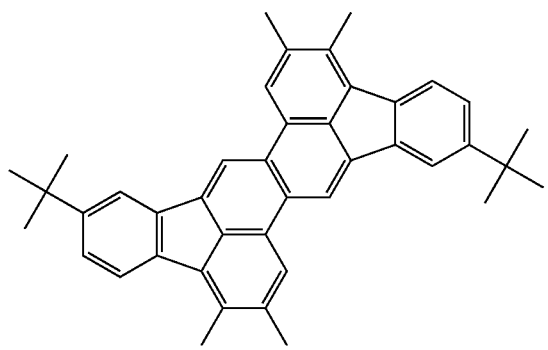
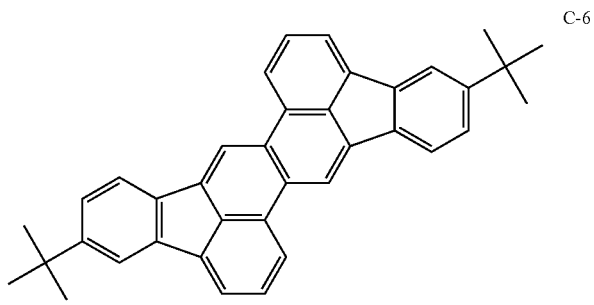
C-6
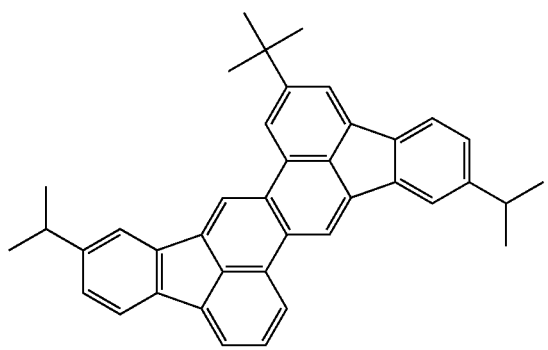
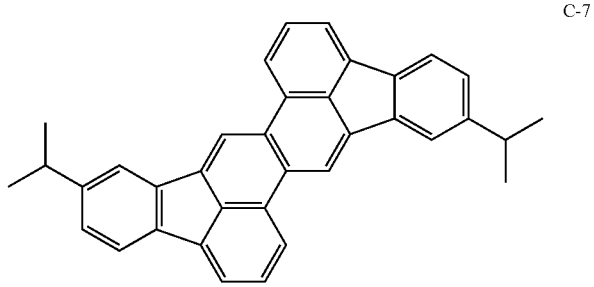
C-7
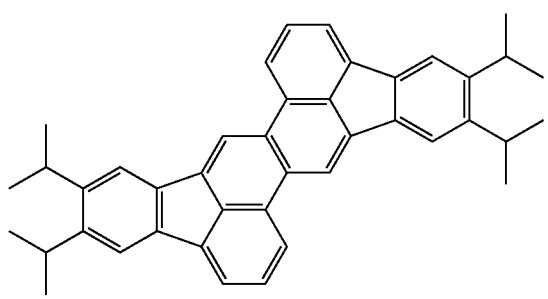
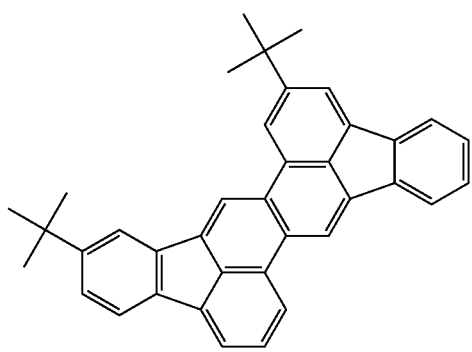
C-9
C-11
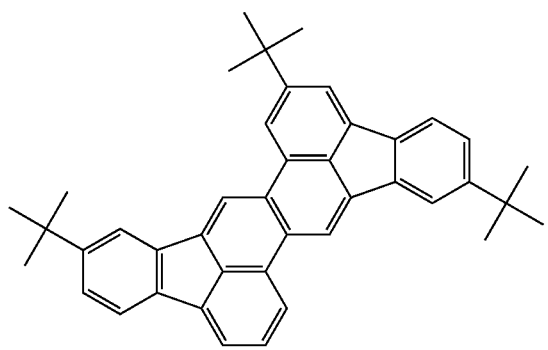
C-12
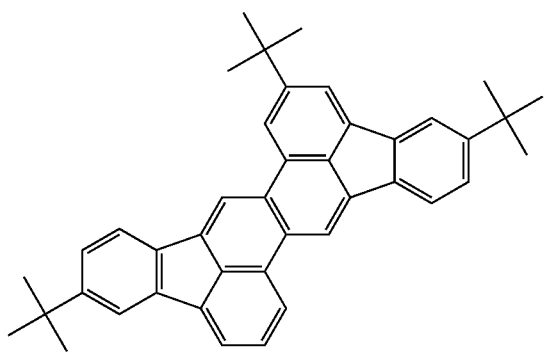

-continued
C-13
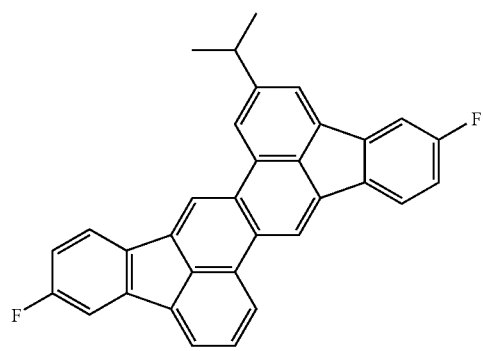
C-14
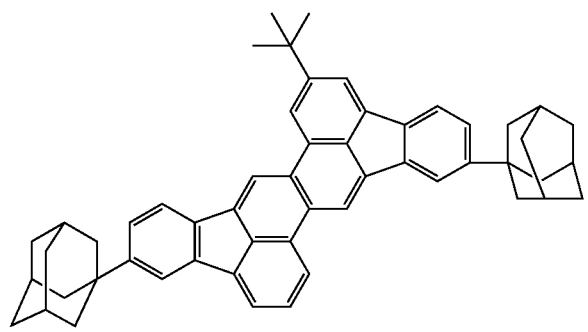
C-15
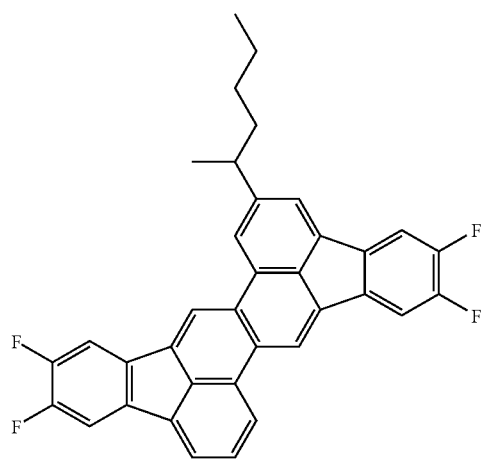
D-1
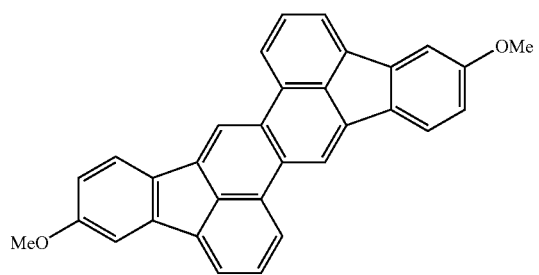
D-2
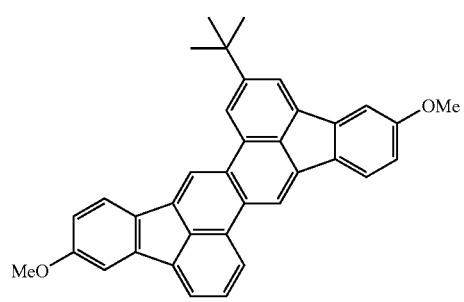
D-3
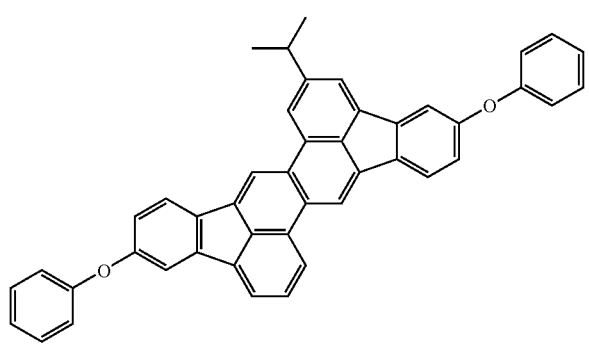
E-1
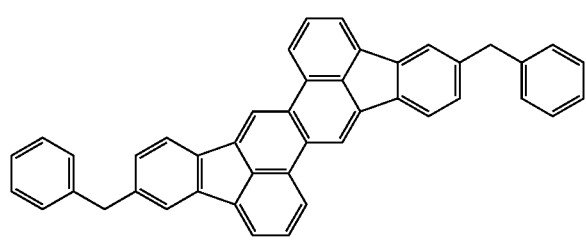
E-2
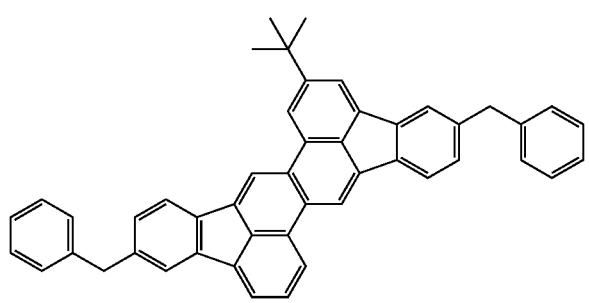

-continued
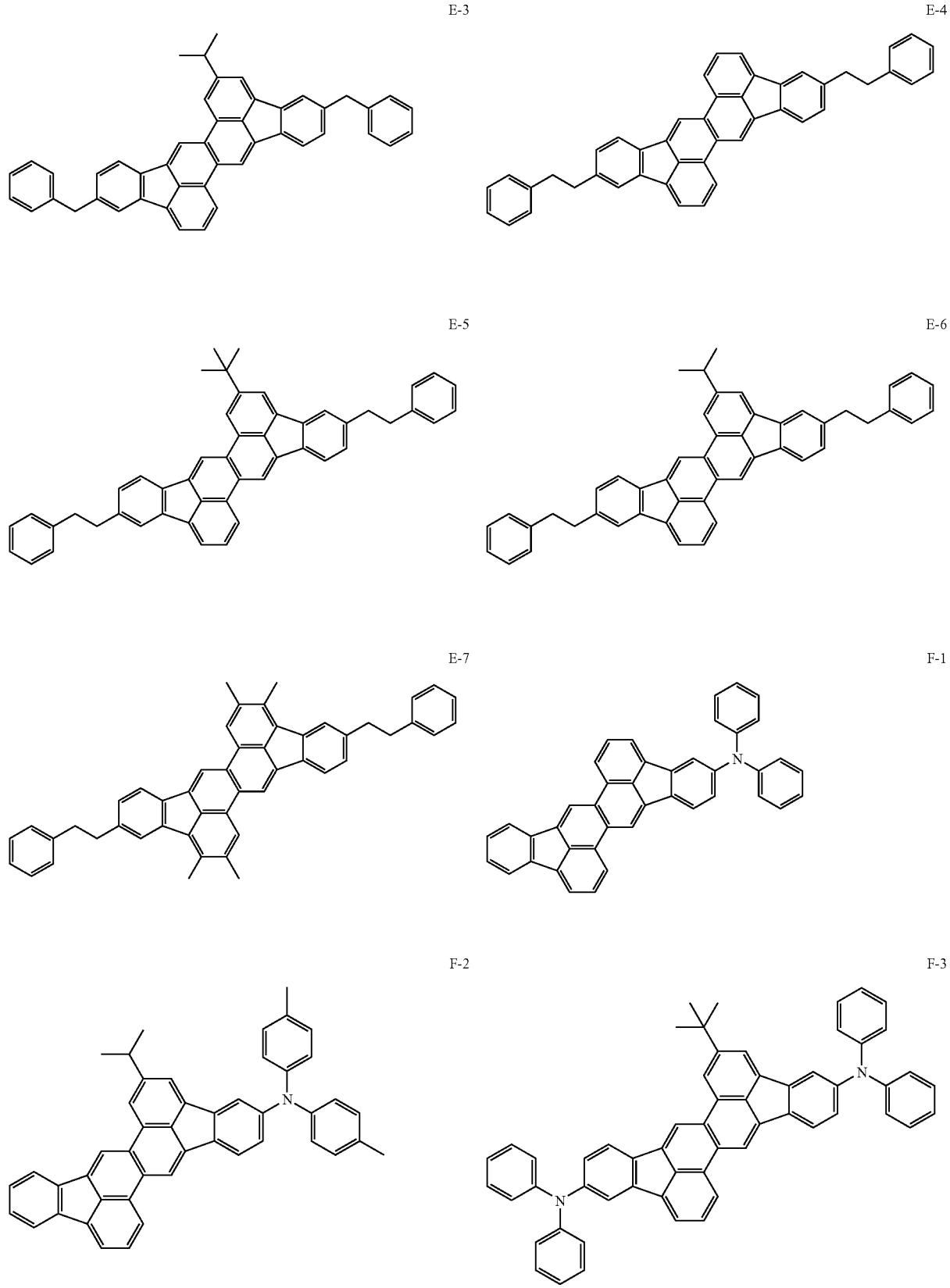

-continued
F-4
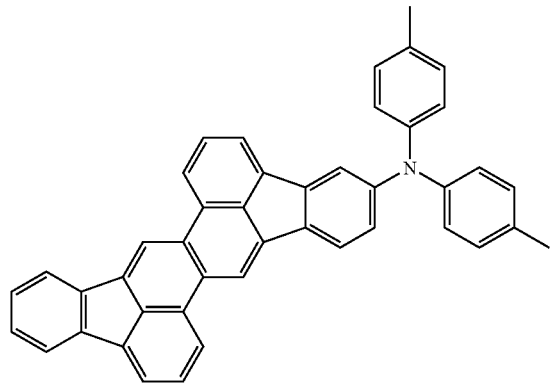
F-5
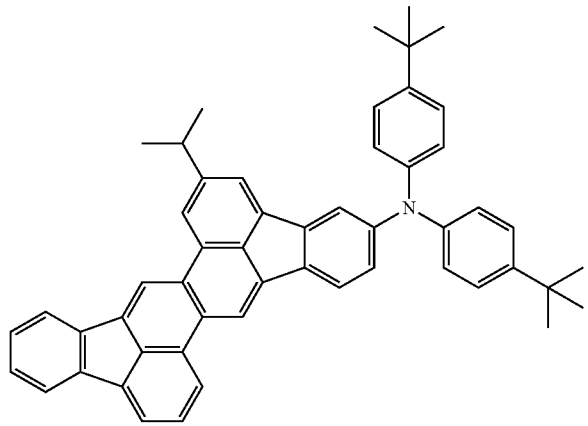
F-6
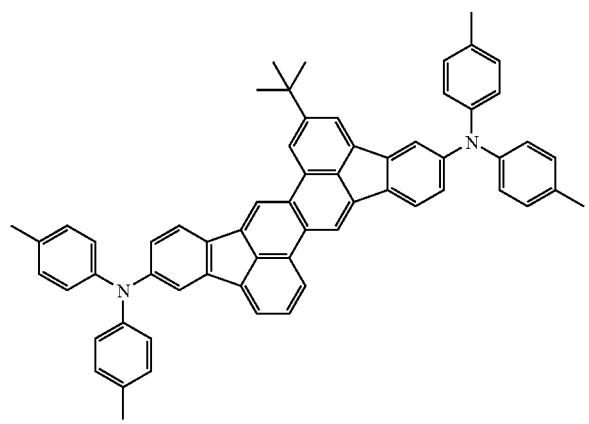
F-7
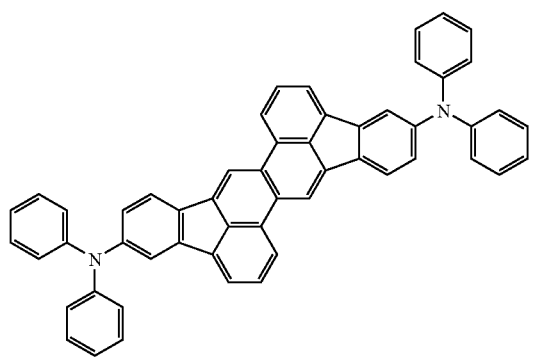
F-8
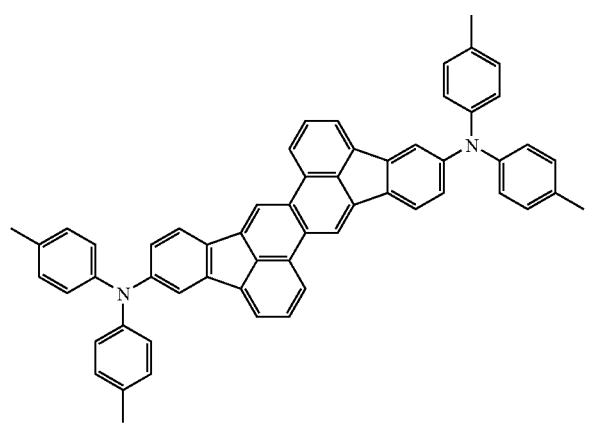
F-9
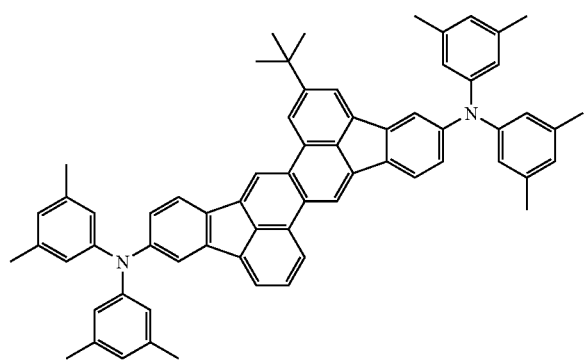

-continued
F-10
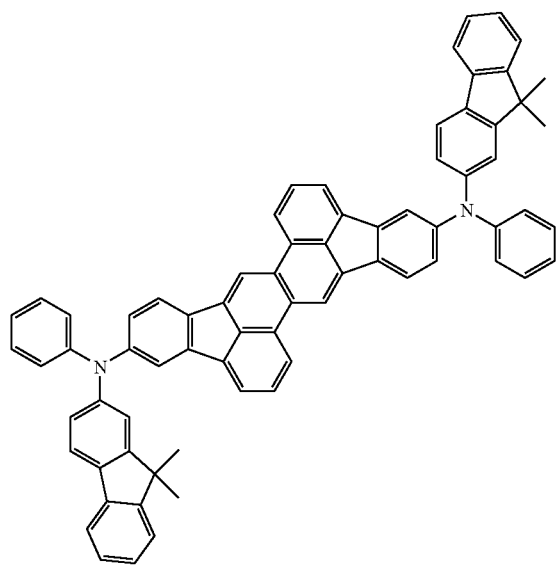
F-11
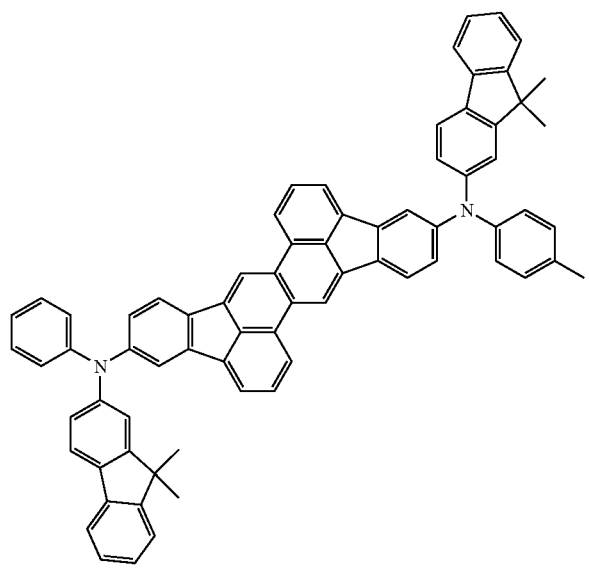
F-12
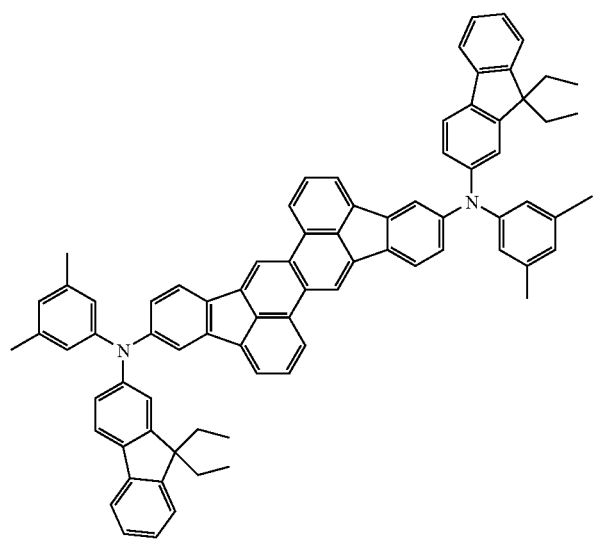
F-13
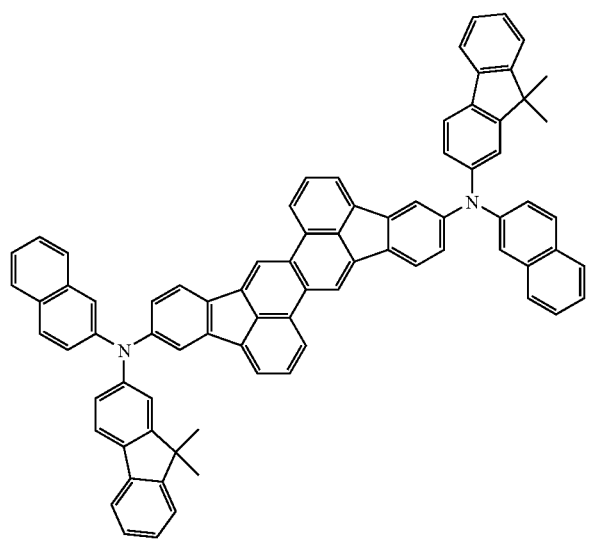
G-1
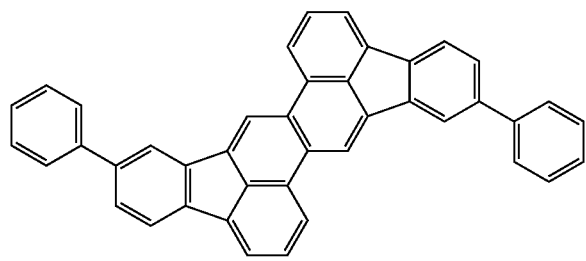
G-2
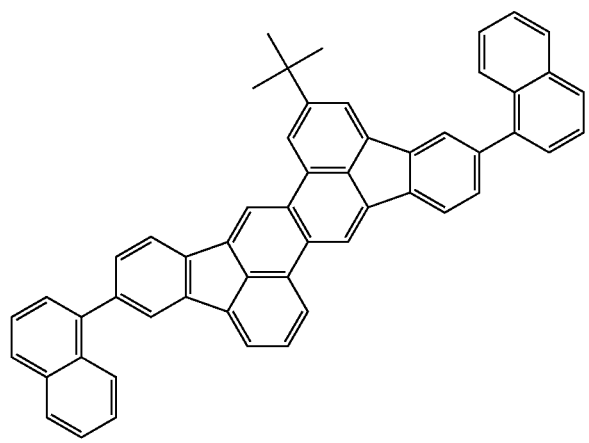

-continued
G-3
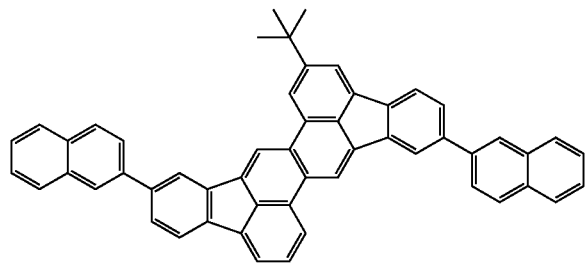
G-4
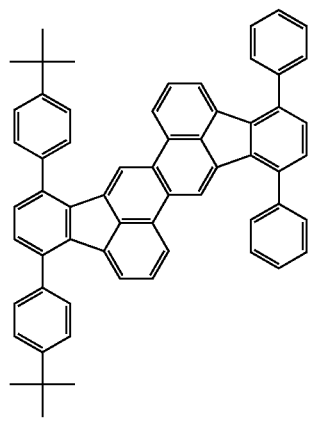
G-5
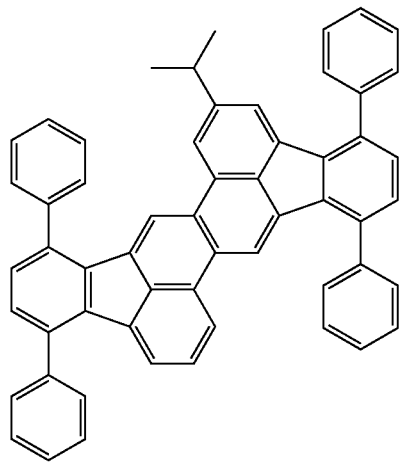
G-6
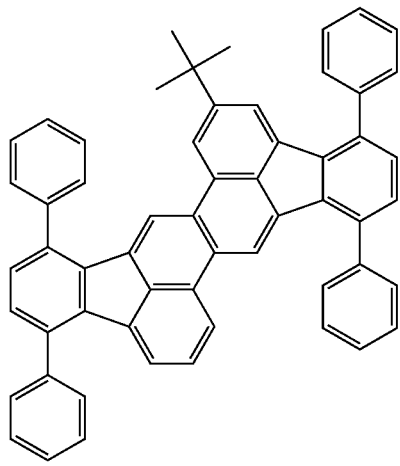
G-7
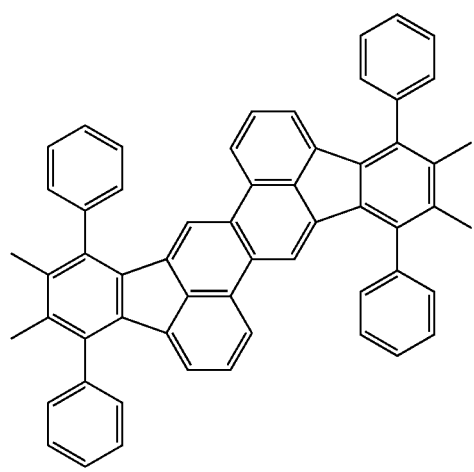
G-8
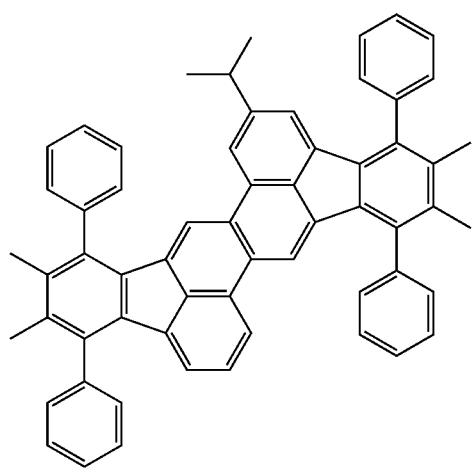

-continued
G-9
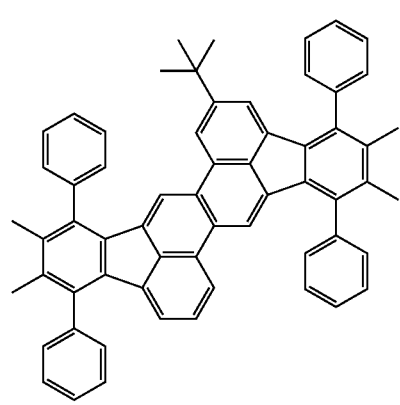
G-10
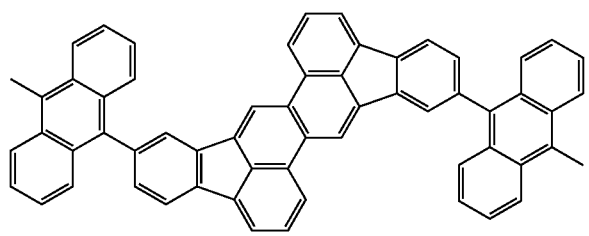
G-11
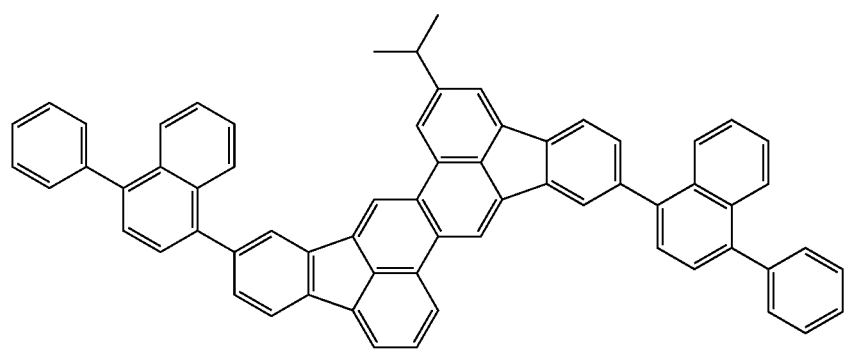
G-12
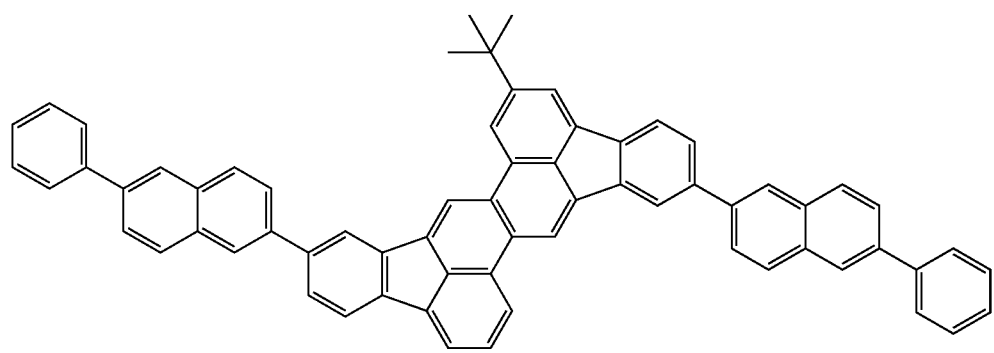
G-13
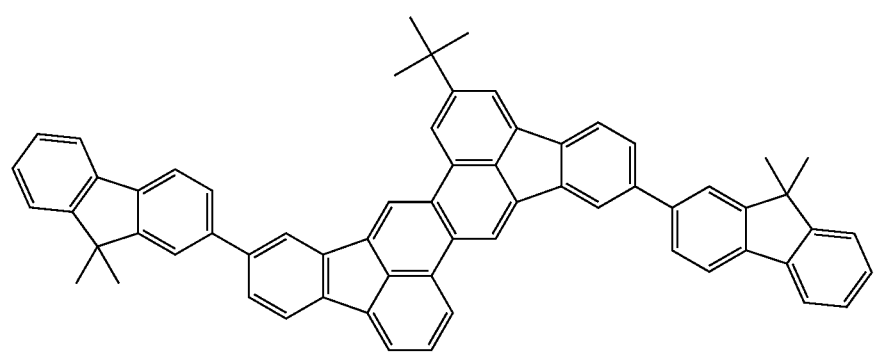

-continued
G-14
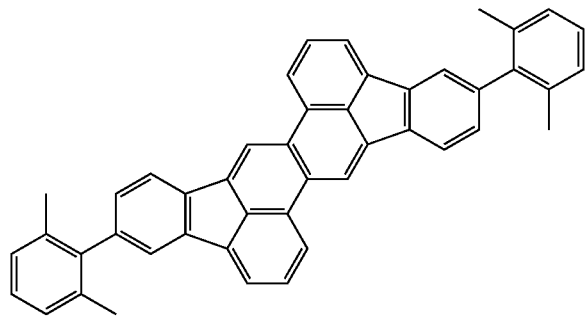
G-15
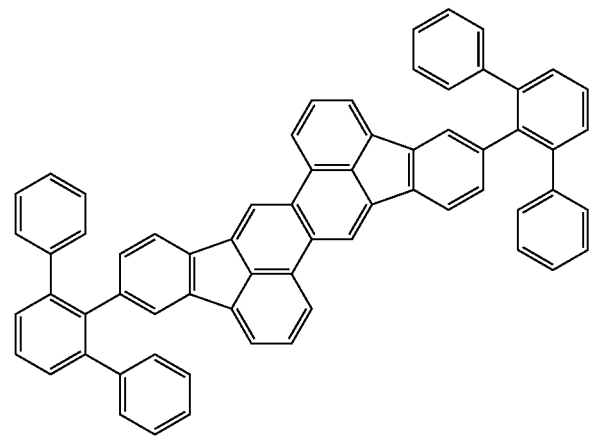
G-16
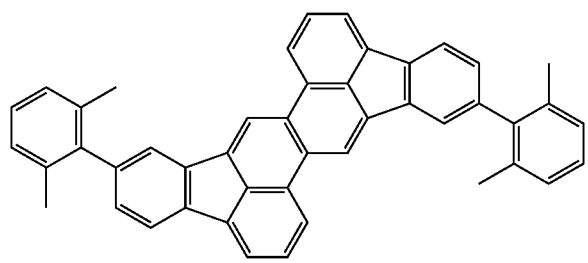
G-17
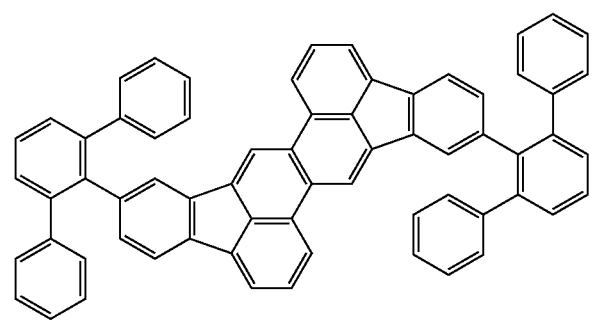
G-18
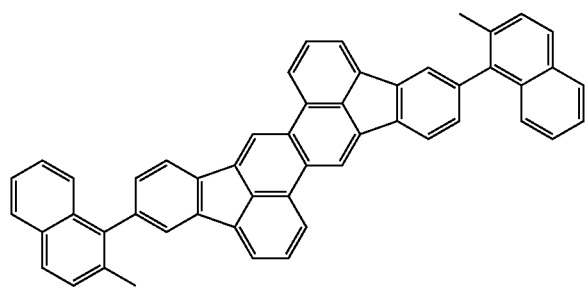
G-19
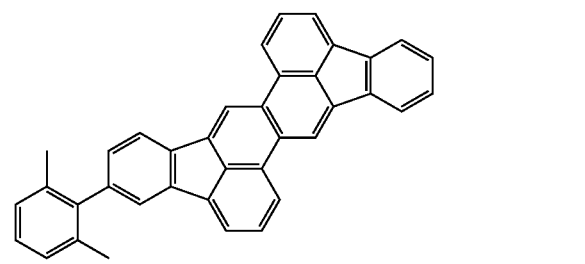
G-20
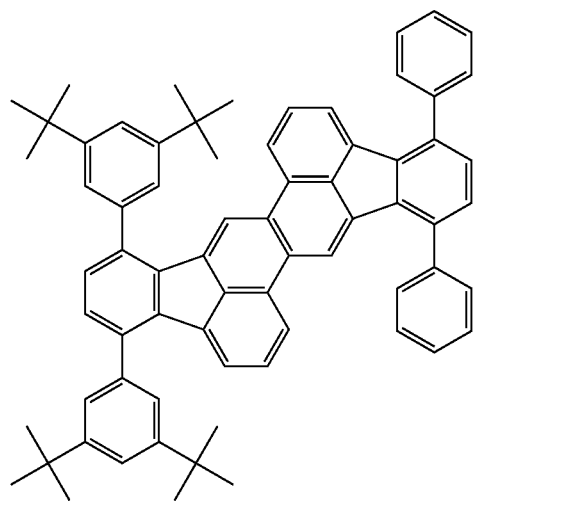
G-21
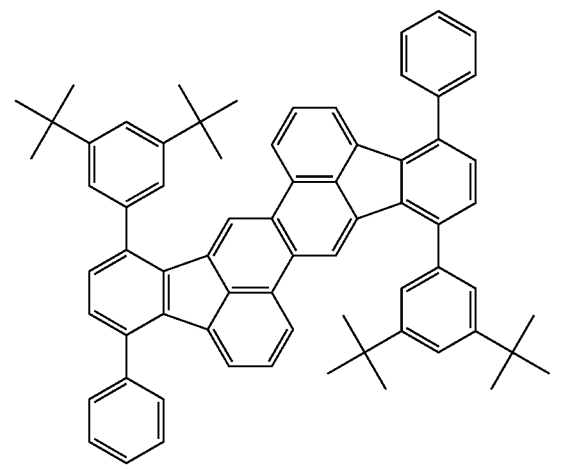

-continued
G-22
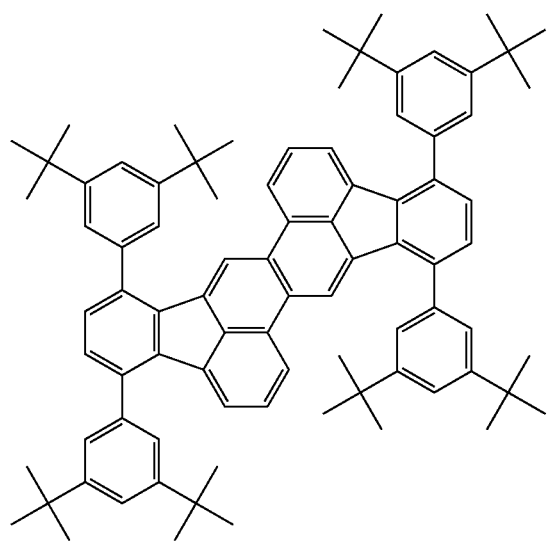
G-23
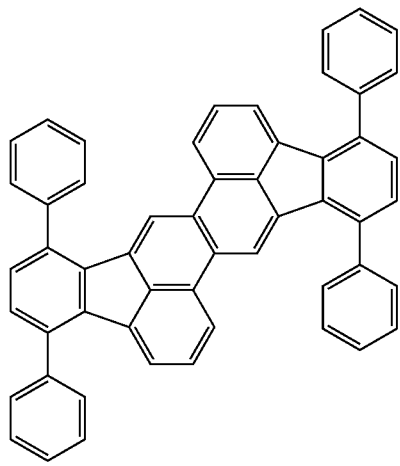
G-24
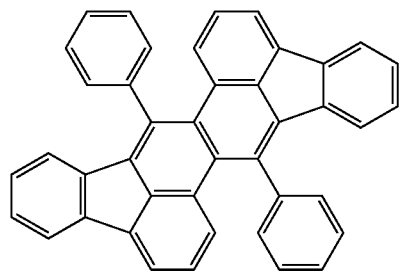
G-25
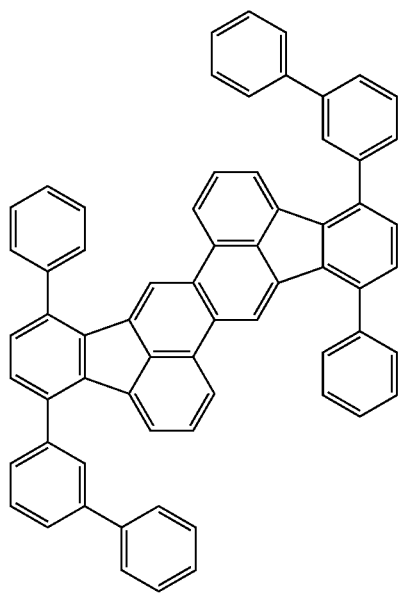
G-26
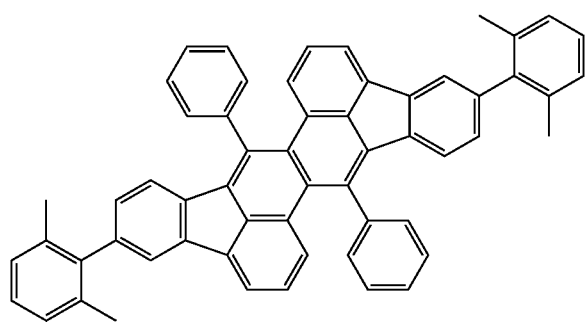
G-27
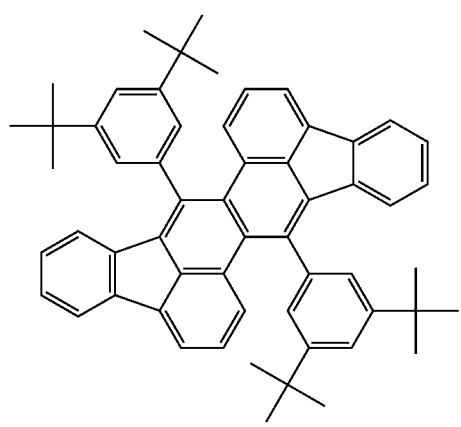

-continued
G-28
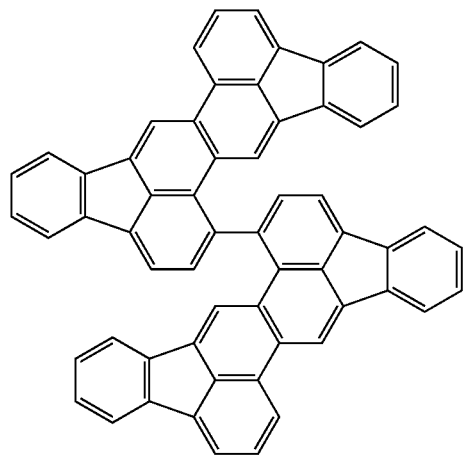
G-29
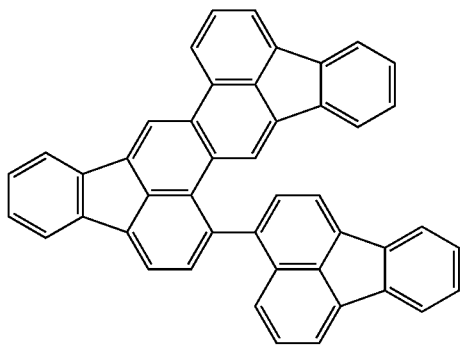
G-30
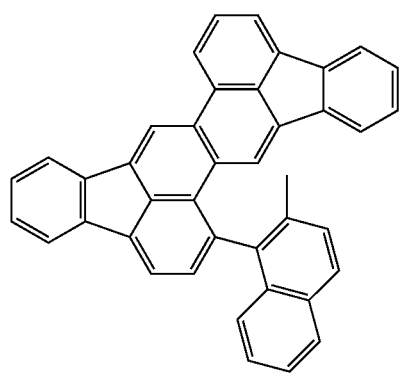
G-31
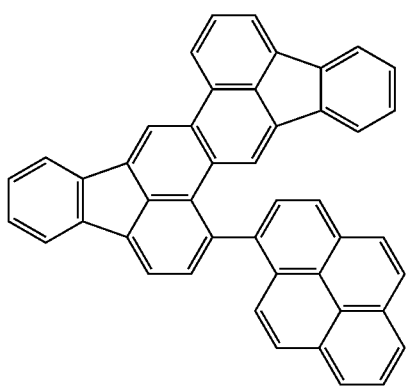
G-32
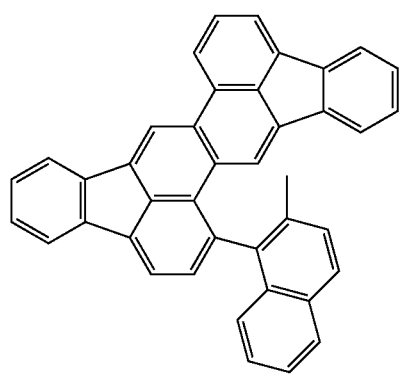

G-33
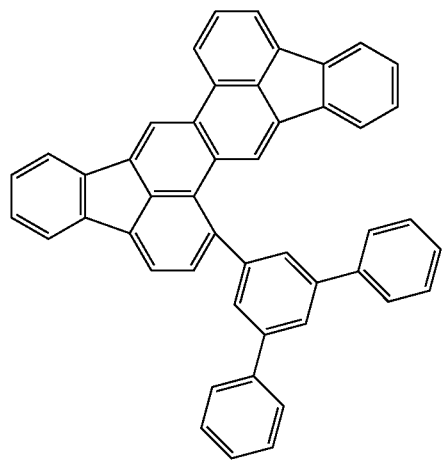
G-34
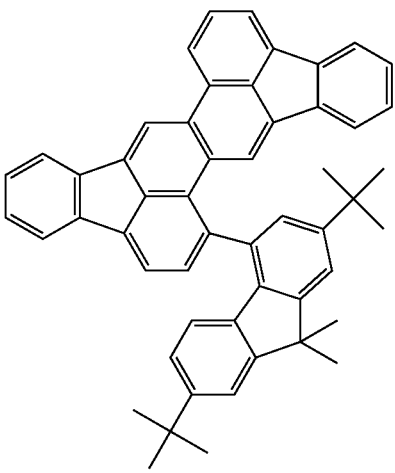
G-35
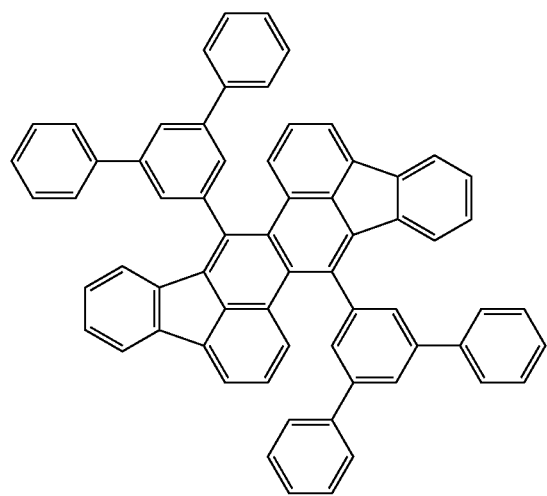
G-36
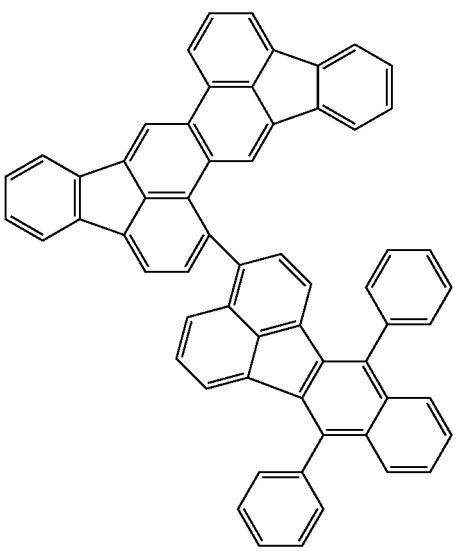
G-37
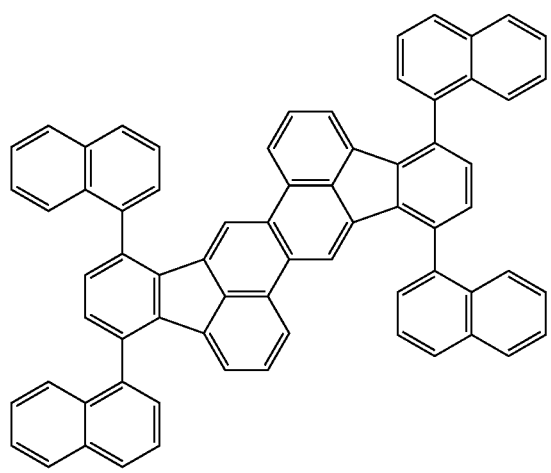
G-38
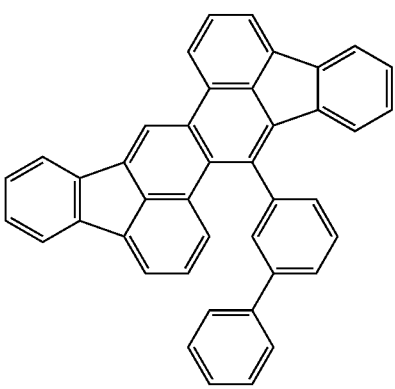

-continued

G-39
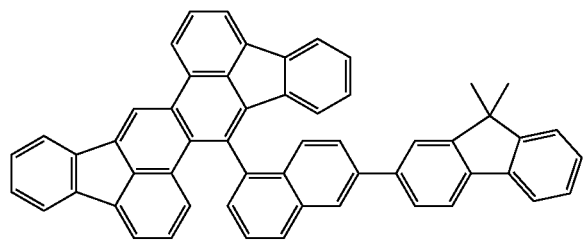

G-40
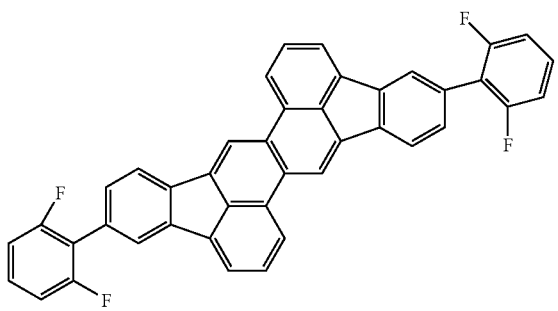

G-41
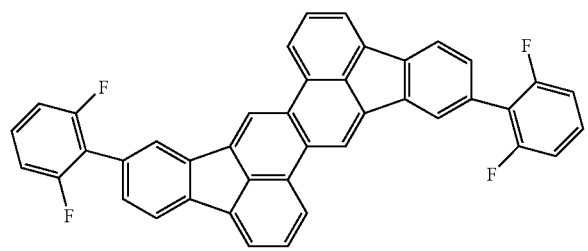

H-1
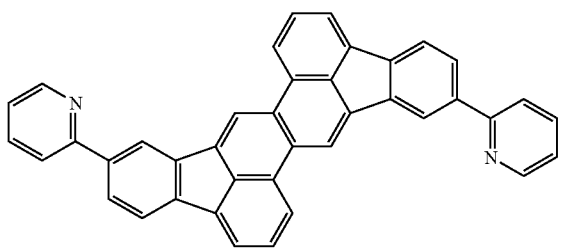

H-2
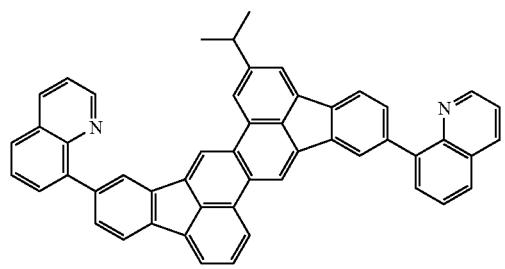

H-3

H-4
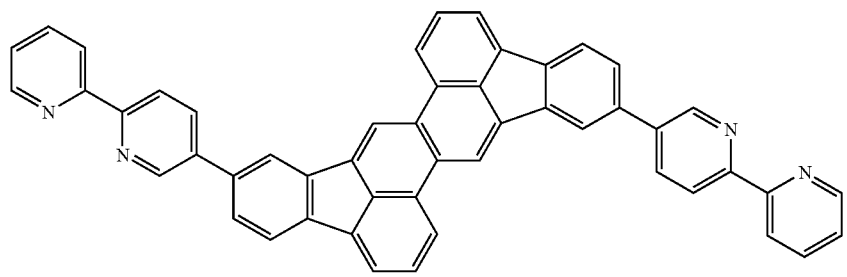

The organic light-emitting device of the present invention will be then specifically described in detail.

The organic light-emitting device of the present invention includes an anode and a cathode, and a layer made of an organic compound interposed between the anode and the cathode. In the organic light-emitting device of the present invention, the layer made of an organic compound contains a condensed ring aromatic compound of the present invention.

The organic light-emitting device of the present invention may have another organic compound layer in addition to the above-described layer made of an organic compound. Examples of another organic compound layer include a hole transporting layer, a hole injecting layer, an electron blocking layer, a hole blocking layer, an electron transporting layer, and an electron injecting layer.

Hereinafter, in reference to figures, the organic light-emitting device of the present invention will be specifically described in detail.

Reference numerals in the figures are first described.

Reference numeral 1 denotes a substrate, reference numeral 2 denotes an anode, reference numeral 3 denotes a light-emitting layer, reference numeral 4 denotes a cathode, reference numeral 5 denotes a hole transporting layer, reference numeral 6 denotes an electron transporting layer, reference numeral 7 denotes a hole injecting layer, and reference numeral 8 denotes a layer for blocking a hole and/or exciton, and reference numerals 10, 20, 30, 40 and 50 respectively denote organic light-emitting devices.

FIG. 1 is a cross-sectional view illustrating a first embodiment of the organic light-emitting device according to the present invention. In the organic light-emitting device 10 in FIG. 1, anode 2, light-emitting layer 3, and cathode 4 are sequentially provided on substrate 1. This organic light-emitting device 10 is useful when light-emitting layer 3 is constituted with an organic compound having all of hole transporting ability, electron transporting ability, and performance of light-emitting property. Furthermore, the organic light-emitting device 10 is also useful when light-emitting layer 3 is constituted by mixing an organic compound having any characteristics of hole transporting ability, electron transporting ability, and performance of light-emitting property.

Figure 2:
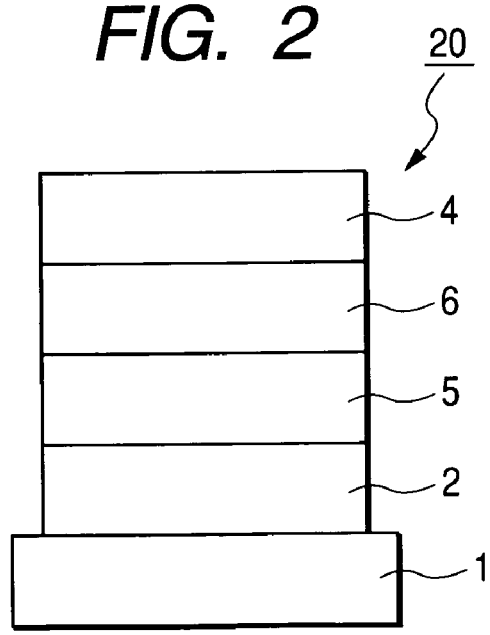
FIG. 2 is a cross-sectional view illustrating a second embodiment of the organic light-emitting device of the present invention.

FIG. 2 is a cross-sectional view illustrating a second embodiment of the organic light-emitting device according to the present invention. In the organic light-emitting device 20 in FIG. 2, anode 2, hole transporting layer 5, electron transporting layer 6 and cathode 4 are sequentially provided on substrate 1. This organic light-emitting device 20 is useful when used combining a light-emitting organic compound having one of hole transporting property and electron transporting property and an organic compound having electron transporting property alone or hole transporting property alone. In addition, in the organic light-emitting device 20, hole transporting layer 5 or electron transporting layer 6 also functions as a light-emitting layer.

Figure 3:
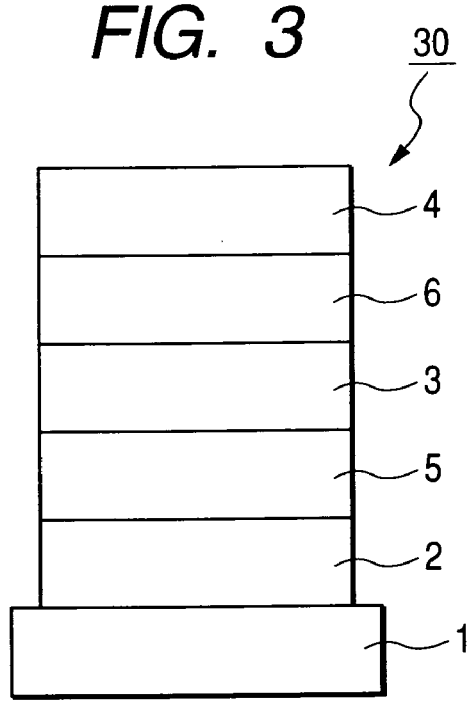
FIG. 3 is a cross-sectional view illustrating a third embodiment of the organic light-emitting device of the present invention.

FIG. 3 is a cross-sectional view illustrating a third embodiment of the organic light-emitting device according to the present invention. The organic light-emitting device 30 in FIG. 3 is configured by inserting light-emitting layer 3 between hole transporting layer 5 and electron transporting layer 6 in the organic light-emitting device 20 in FIG. 2. In this organic light-emitting device 30, functions of carrier transportation and light emission are separated, organic compounds having respective characteristics such as hole transporting property, electron transporting property and light emitting property can be used with suitable combination. Accordingly, flexibility of material selection is extremely increased, and various organic compounds having different light emitting wavelengths can be used, which thus enables diversification of color hue of light emission. Furthermore, it enables the organic light-emitting device 30 to intend improvement in light-emitting efficiency by effectively blocking a carrier or exciton in light-emitting layer 3 on the center.

Figure 4:
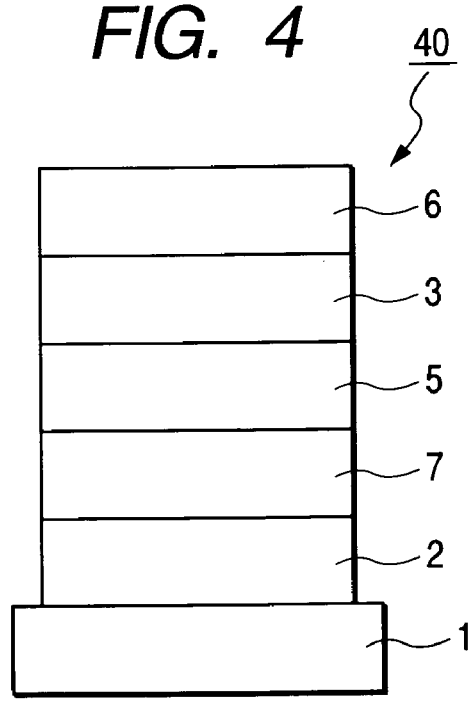
FIG. 4 is a cross-sectional view illustrating a fourth embodiment of the organic light-emitting device of the present invention.

FIG. 4 is a cross-sectional view illustrating a fourth embodiment of the organic light-emitting device according to the present invention. The organic light-emitting device 40 in FIG. 4 is configured by providing hole injecting layer 7 between anode 2 and hole transporting layer 5 in the organic light-emitting device 30 in FIG. 3. This organic light-emitting device 40 is effective for having a low voltage since hole injecting layer 7 is provided, thereby improving adhesion between anode 2 and hole transporting layer 5 or hole injecting property.

Figure 5:
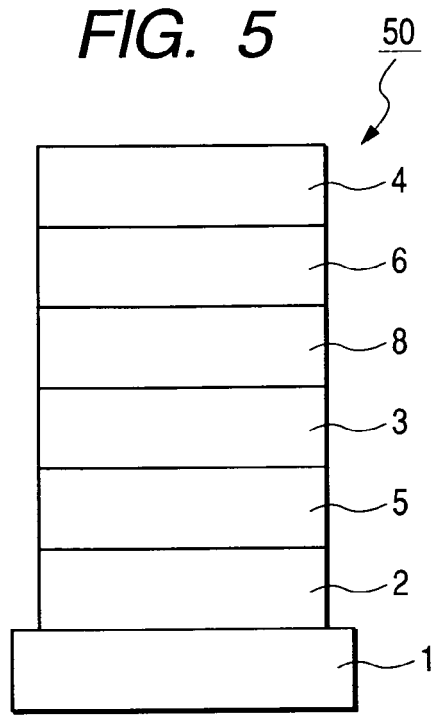
FIG. 5 is a cross-sectional view illustrating a fifth embodiment of the organic light-emitting device of the present invention.

FIG. 5 is a cross-sectional view illustrating a fifth embodiment of the organic light-emitting device according to the present invention. The organic light-emitting device 50 in FIG. 5 is configured by inserting a layer of inhibiting a hole or exciton passing through to the side of cathode 4 (hole/exciton blocking layer 8) between light-emitting layer 3 and electron transporting layer 6. By using an organic compound having extremely high ionization potential as hole/exciton blocking layer 8, light-emitting efficiency of the organic light-emitting layer 50 is improved.

However, the above described first to fifth embodiments are only very basic device structures, and a structure of the organic light-emitting device using a condensed rung aromatic compound of the present invention is not limited to these structures. For example, an insulating layer, an adhering layer or an interfering layer can be provided on an interface of an organic layer with an electrode, and a hole transporting layer can be formed from various layer structures constituted with double layers having different ionization potentials.

The condensed ring aromatic compound of the present invention can be used in any of the above described first to fifth embodiments. When the condensed ring aromatic compound of the present invention is used, a single compound may be used, or a plurality of compounds may be used in combination.

The condensed ring aromatic compound of the present invention is contained in any of a later made of an organic compound, for example, light emitting layer 3, hole transporting layer 5, electron transporting layer 6, hole injecting layer 7 and hole/exciton blocking layer 8 in the first to fifth embodiments. The condensed ring aromatic compound is preferably contained in light-emitting layer 3. The condensed ring aromatic compound of the present invention contained in these layers may be one kind or may be two or more kinds.

Light-emitting layer 3 is preferably formed from a host and a guest. Herein, when light-emitting layer 3 is formed from a host and a guest having carrier transporting property, main processes reaching light emission contain the following several steps.

1. Transportation of electron and hole in a light-emitting layer
2. Production of exciton of host
3. Excitation energy transmission among host molecules
4. Excitation energy transfer from host to guest Desired energy transfer and light emission in each step occur in competition with various deactivation processes.

In order to enhance light-emitting efficiency of an organic light-emitting device, it goes without saying that light-emitting quantum efficiency of a light-emitting center material itself is increased. However, it is a large factor how effectively energy transfer between host and host or between host and guest can be made. Cause of deterioration in light emission due to energization is not clear at this time, however, it is supposed that at least environmental changes of a light-emitting center material itself or a light-emitting material due to its peripheral molecules are involved.

When the condensed ring aromatic compound of the present invention is used for a host or a guest, light-emitting efficiency of a device, luminance of light output by the device, and durability of the device are improved.

When the condensed ring aromatic compound of the present invention is used in the organic light-emitting device of the present invention as a material for a light-emitting layer, the light-emitting layer can be constituted only by the condensed ring aromatic compound of the present invention. Furthermore, the condensed ring aromatic compound of the present invention can be used as a guest (dopant) material or a host material.

Herein, when the condensed ring aromatic compound of the present invention is used as a guest material, the amount to be used is preferably 0.01% by weight to 20% by weight based on a host material, more preferably 0.1% by weight to 15% by weight. Using the condensed ring aromatic compound of the present invention in this range can appropriately inhibit concentration quenching caused by overlapping each of guests in a light-emitting layer.

When the condensed ring aromatic compound of the present invention is used as a guest material, it is preferred that the energy gap of a host material is greater than the energy gap of the guest.

In the present invention, particularly, the condensed ring aromatic compound of the present invention is used as a constituting material of the light-emitting layer, conventionally known low molecular weight and polymer hole transporting compounds, light-emitting compounds, electron transporting compounds, and the like can be used together according to necessity.

Examples of the hole transporting compound include triarylamine derivatives, phenylene diamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, porphyrin derivatives, poly(vinylcarbazole), poly(silylene), poly(thiophene), and other conductive polymers.

Examples of the light-emitting compound include, in addition to the condensed ring aromatic compound of the present invention, naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, rubrene derivatives, quinacridone derivatives, acridone derivatives, coumarin derivatives, pyran derivatives, nile red, pyrazine derivatives, benzimidazole derivatives, benzothiazole derivatives, bonzoxazole derivatives, stilbene derivatives, and organic metal complex (for example, organic aluminum complex such as tris(8-quinolinolato)aluminum, and organic beryllium complex), and polymer derivatives such as poly(phenylenevinylene) derivatives, poly(fluorene) derivatives, poly(phenylene) derivatives, poly(thienylenevinylene) derivatives, and poly(acetylene) derivatives.

Examples of the electron transporting compound include oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derovatives, phenanthrolene derivatives, and organic metal complex.

Examples of materials constituting an anode include elemental substances of metals such as gold, platinum, silver, copper, nickel, palladium, cobalt, serene, vanadium and tungsten, or alloys thereof, and metallic oxides such as tin oxide, zinc oxide, indium oxide, indium tin oxide (ITO), and indium zinc oxide. Furthermore, other examples include conductive polymers such as polyaniline, polypyrrole, polythiophene, and polyphenylene sulfide. These electrode substances can be used alone, or a plurality of these may be used in combination. In addition, the anode may be formed from a monolayer structure, or can be formed from a multilayer structure.

Examples of materials constituting cathode include elemental substances of metals such as lithium, sodium, potassium, calcium, magnesium, aluminium, indium, ruthenium, titanium, manganese, yttrium, silver, lead, tin and chromium. Alternatively, other examples include a plurality of alloys such as lithium-indium, sodium-potassium, magnesium-silver, aluminum-lithium, aluminum-magnesium, and magnesium-indium. Furthermore, examples include metallic oxides such as indium tin oxide (ITO). These electrode substances can be used alone, or a plurality of these may be used in combination. In addition, the cathode may be formed from a monolayer structure, or can be formed from a multilayer structure.

A substrate used in the organic light-emitting device of the present invention is not particularly limited, and translucent substrates such as a metallic substrate and a ceramic substrate, and transparent substrates such as glass, quartz, and a plastic sheet are used.

It is also possible to control chromogenic light by using a color filter film, a fluorescent color conversion filter film, a dielectric reflective film, or the like for a substrate. Further, it is possible to produce a thin film transistor (TFT) on the substrate and connect thereto to produce a device.

In terms of a direction of taking out light by the device, both of structures are possible: a bottom emission structure (a structure of taking out light from the side of the substrate) and top emission (a structure of taking out light from the opposite side of the substrate).

Examples

Hereinafter, the present invention will be more specifically described in reference to examples, however, the present invention is not limited to these Examples.

Example 1

Synthesis of Exemplified Compound A-1

(1-1) Synthesis of Synthetic Intermediate Compound 1-3

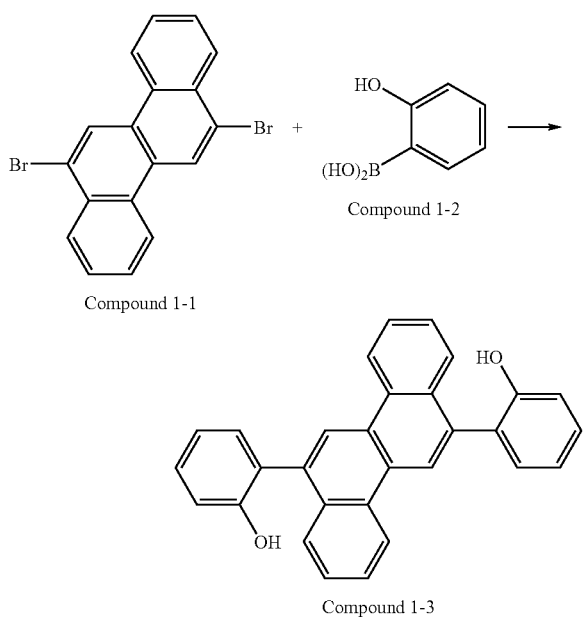

Compound 1-1

Compound 1-2

Compound 1-3

The following reagents and solvent were charged in a 300 ml-recovery flask, and stirred under a nitrogen flow at 60° C. for 8 hours.

Compound 1-1: 1.3 g (4.05 mmol)

Compound 1-2: 1.22 g (8.90 mmol)

Tetrakistriphenylphosphine palladium (0): 519 mg (0.45 mmol)

Toluene: 100 ml

Ethanol: 50 ml 2M-sodium carbonate aqueous solution: 20 ml

After completion of the reaction, ethyl acetate and water were added to separate the organic layer, dried over magnesium sulfate, and then the solvent was distilled off. Purification was carried out by silica gel column chromatography (developing solvent: toluene/heptane=1/1), and 1.3 g of the compound 1-3 (yield 78%) was obtained.

(1-2) Synthesis of Synthetic Intermediate Compound 1-4

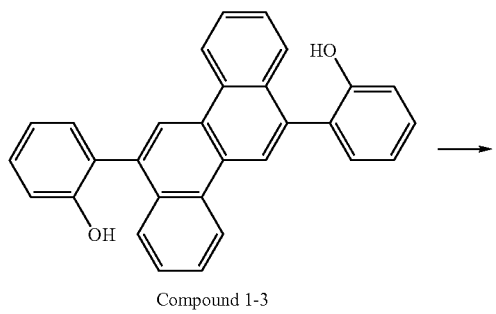

Compound 1-3

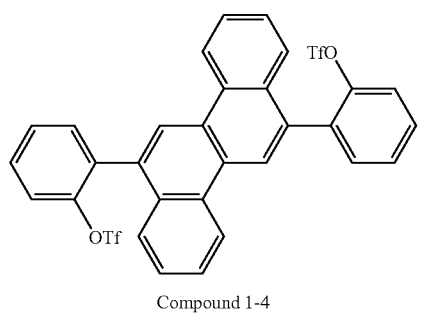

Compound 1-4

The following reagents, solvent and the like were charged in a recovery flask, and stirred in a cooling bath at −20° C. for 30 minutes.

Compound 1-3: 1.3 g (3.15 mmol)

Chloroform: 100 ml

Triethylamine: 2 ml

Then, 1.58 ml (9.45 mmol) of trifluoromethanesulfonic anhydride was slowly dropped thereto, and stirred at room temperature for 6 hours. After completion of the reaction, ethyl acetate and water were added to separate the organic layer, dried over magnesium sulfate, and then the solvent was distilled off. Purification was carried out by silica gel column chromatography (developing solvent: toluene/heptane=1/2), and 1.74 g (yield 82%) of the compound 1-4 was obtained.

(1-3) Synthesis of Exemplified Compound A-1

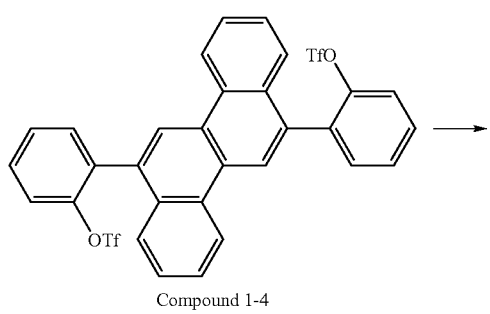

Compound 1-4

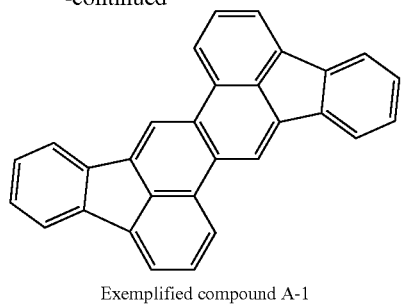

Exemplified compound A-1

The following reagents, solvent and the like were charged in a recovery flask, and stirred under a nitrogen flow at 80° C. for 8 hours.

Compound 1-4: 270 mg (0.4 mmol)

LiCl: 100 mg (2.4 mmol)

1,8-diazabicyclo [5.4.0] 7-undecene: 146 mg (0.96 mmol)

Bistriphenylphosphine palladium (II) dichloride: 40 mg (0.04 mmol)

Dimethylformamide: 50 ml

After completion of the reaction, ethyl acetate and water were added to separate the organic layer, dried over magnesium sulfate, and then the solvent was distilled off. Purification was carried out by silica gel column chromatography (developing solvent: toluene/heptane=1/3), and 72 mg (yield 48%) of the exemplified compound A-1 was obtained.

With respect to the obtained compound, the physical properties thereof were measured and evaluated.

(Molecular Weight)

It was confirmed that M+was 376.4 by MALDI-TOF-MS (matrix-assisted laser deposition ionization—time of flight mass spectrometry), and the exemplified compound A-1 was identified.

(NMR)

The structure of this exemplified compound A-1 was confirmed by NMR measurement.

$^1$H-NMR (THF-d8, 400 MHz) σ (ppm): 9.36 (s, 2H), 8.80 (d, 2H, J=8.0 Hz), 8.18-8.16 (m, 2H), 8.07 (d, 2H, J=8.0 Hz), 7.97-7.95 (m, 2H), 7.82 (m, 2H), 7.38 (m, 4H)

(Melting Point)

It was confirmed that a melting point of the exemplified compound A-1 was 378° C. by differential scanning calorimetry (DSC).

(Light-Emitting Characteristics)

Figure 6:
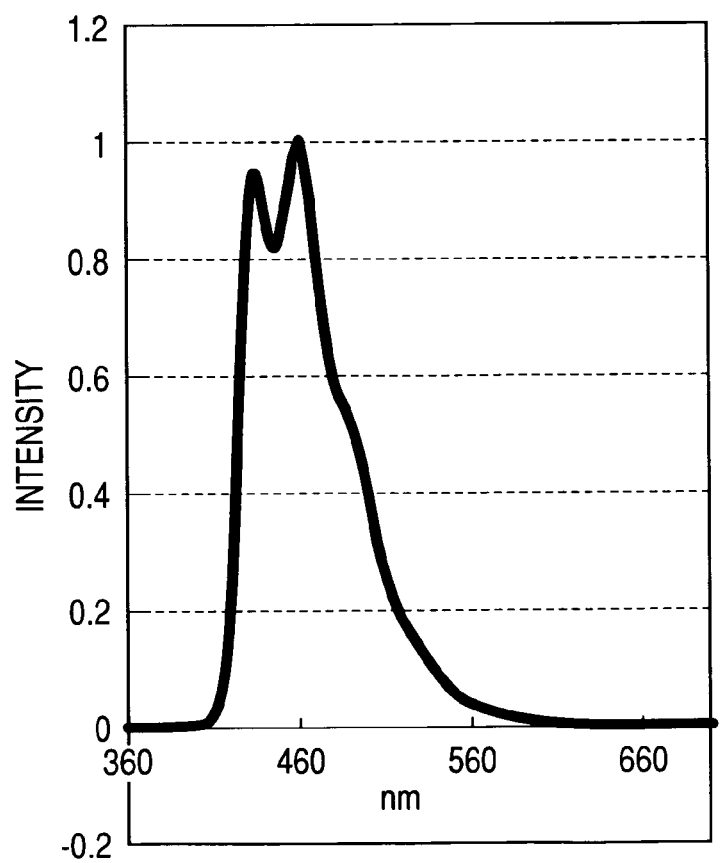
FIG. 6 is a view illustrating a PL spectrum (excitation wavelength: 340 nm) of a toluene solution ($1\times10^{-5}$ mol/l) of an exemplified compound A-1.

Light emission spectrum of the exemplified compound A-1 in a solution state was measured. For measurement of the light emission spectrum, an absorption spectrum of a toluene solution ($1\times10^{-5}$ mol/l) of the exemplified compound A-1 was measured using a spectrophotometer U-3010 (manufactured by Hitachi, Ltd.) in advance. After measuring the absorption spectrum, a light emission spectrum of the toluene solution ($1\times10^{-5}$ mol/l) of the exemplified compound A-1 was measured using a spectrophotometer F-4500 (manufactured by Hitachi, Ltd.). Herein, as a result of the measurement of the absorption spectrum, an excitation wavelength was determined to be 340 nm. As a result of the measurement, PL spectrum shown in FIG. 6 was obtained. According to the PL spectrum shown in FIG. 6, the first peak and the second peak of maximum light-emitting wavelength of the exemplified compound A-1 were respectively 436 nm and 461 nm, and found to show preferable blue light emission.

A quantum efficiency of the exemplified compound A-1 in a toluene solution ($1\times10^{-5}$ mol/l) was measured, and as a result, a high value such as 0.91 was shown. In addition, in the measurement of the quantum efficiency, values are calculated using fluoranthene as a comparative control compound in comparison. A quantum efficiency in a diluted solution of fluoranthene is 0.35 (Steven L, Murov., Handbook of Phtochemistry, Second Edition, Revised and Expanded, (1993)).

Example 2

Synthesis of Exemplified Compound C-6

Exemplified compound C-6 was synthesized in the same synthesis method as Example 1. Specifically, the synthesis was carried out under the same conditions in Example 1 except for changing compound 1-2 to compound 1-5.

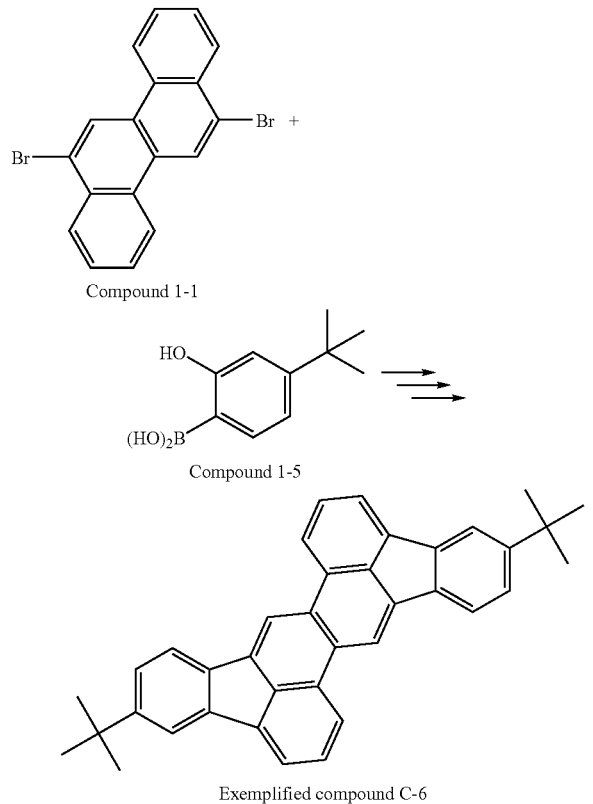

With respect to the obtained compound, the physical properties thereof were measured and evaluated.
(Molecular Weight)
It was confirmed that M+ was 488.6 by MALDI-TOF-MS (matrix-assisted laser deposition ionization—time of flight mass spectrometry), and the exemplified compound C-6 was identified.
(NMR)
The structure of this exemplified compound C-6 was confirmed by NMR measurement.
$^1$H-NMR (CDCl$_3$, 400 MHz) σ (ppm): 9.15 (s, 2H), 8.69 (d, 2H, J=8.0 Hz), 8.08-8.01 (m, 6H), 7.87-7.83 (m, 2H), 7.52-7.48 (m, 2H), 1.54 (s, 18H)
(Melting Point)
It was confirmed that a melting point of the exemplified compound C-6 was 459° C. by differential scanning calorimetry.

Figure 7:
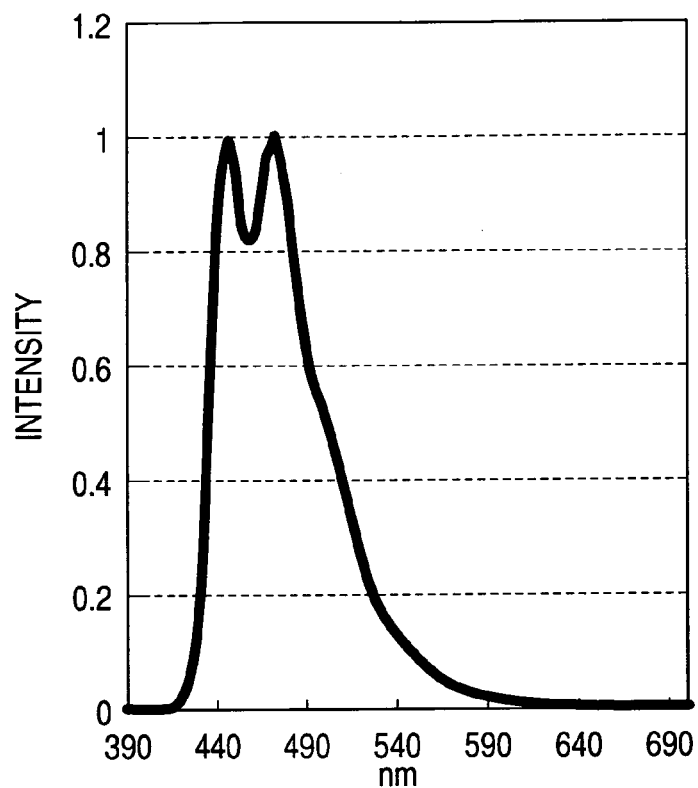
FIG. 7 is a view illustrating a PL spectrum (excitation wavelength: 355 nm) of a toluene solution ($1\times10^{-5}$ mol/l) of an exemplified compound C-6.
Figure 8:
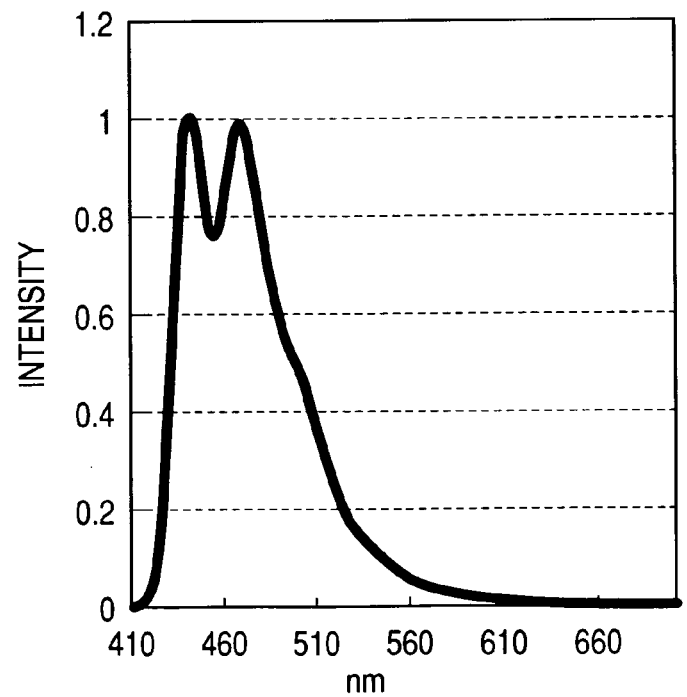
FIG. 8 is a view illustrating a PL spectrum (excitation wavelength: 355 nm) of a toluene solution ($1\times10^{-5}$ mol/l) of an exemplified compound G-14.
Figure 9:
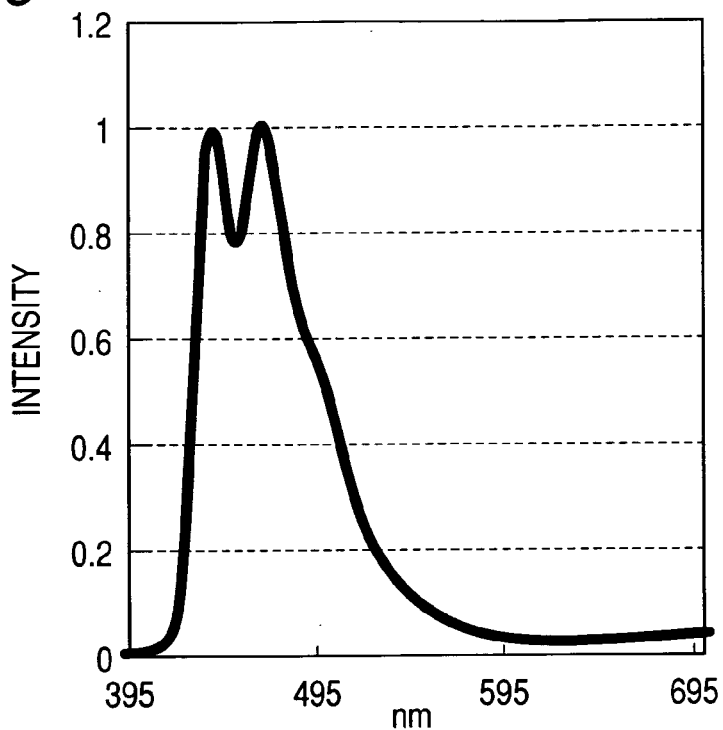
FIG. 9 is a view illustrating a PL spectrum (excitation wavelength: 355 nm) of a toluene solution ($1\times10^{-5}$ mol/l) of an exemplified compound G-19.
Figure 10:
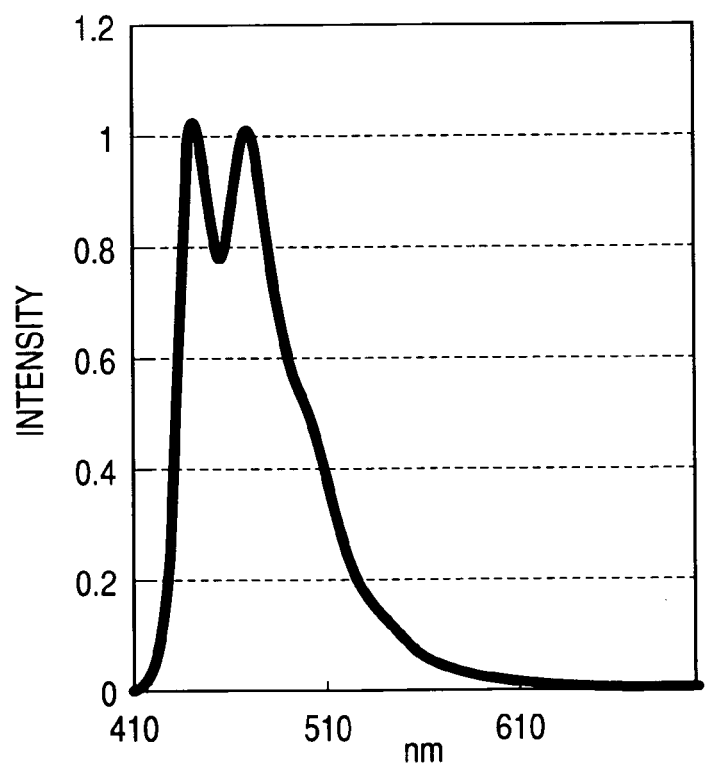
FIG. 10 is a view illustrating a PL spectrum (excitation wavelength: 355 nm) of a toluene solution ($1\times10^{-5}$ mol/l) of an exemplified compound G-18.

(Light-Emitting Characteristics)
Absorption spectrum of a toluene solution (1×10$^{-5}$ mol/l) of the exemplified compound C-6 in a solution state was measured. After measuring the absorption spectrum, a light emission spectrum (PL spectrum) of the toluene solution (1×10$^{-5}$ mol/l) of the exemplified compound C-6 was measured. Herein, as a result of the measurement of the absorption spectrum, an excitation wavelength was determined to be 355 nm. As a result of the measurement, PL spectrum shown in FIG. 7 was obtained. According to the PL spectrum shown in FIG. 7, the first peak and the second peak of maximum light-emitting wavelength of the exemplified compound C-6 were respectively 446 nm and 472 nm, and found to show preferable blue light emission.

Example 3

Synthesis of Exemplified Compounds G-14 and G-19

(3-1) Synthesis of Synthetic Intermediate Compound 1-6

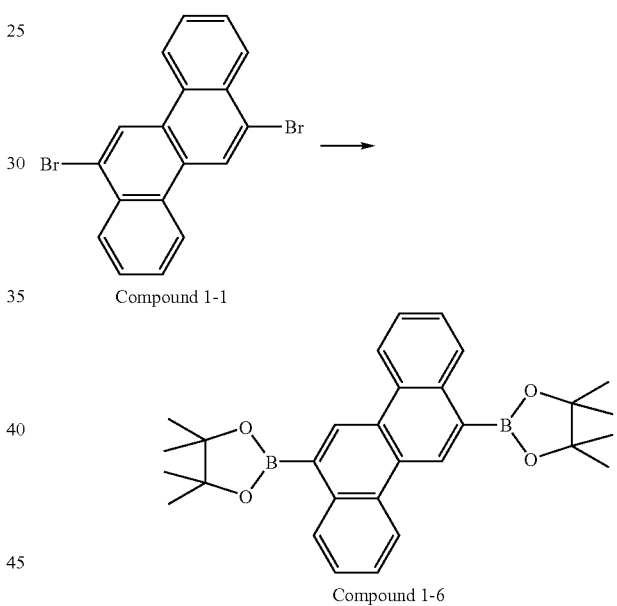

The following reagents and solvent were charged in a 300 ml-recovery flask, and stirred under a nitrogen flow at 80° C. for 8 hours.
Compound 1-1: 2.5 g (6.48 mmol)
4,4,5,5-tetramethyl-1,3,2-dioxaborolane: 5.63 ml (38.8 mmol)
[1,3-bis(diphenylphosphino)propane]dichloronickel II): 325 mg (0.65 mmol)
Toluene: 100 ml
Triethylamine: 30 ml
After completion of the reaction, the temperature was cooled to room temperature, and water was then added thereto. An aqueous ammonium chloride solution was further added and stirred for 3 hours. Then, ethyl acetate and water were added to separate the organic layer, dried over magnesium sulfate, and then the solvent was distilled off. Purification was carried out by silica gel column chromatography (developing solvent: toluene), and 2.1 g (yield 68%) of the compound 1-6 was obtained.

(3-2) Synthesis of Synthetic Intermediate Compound 1-8

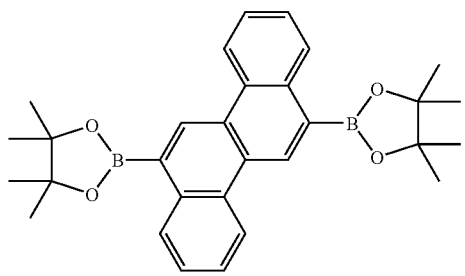

Compound 1-6

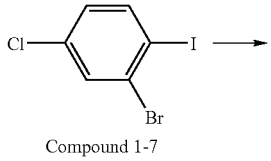

Compound 1-7

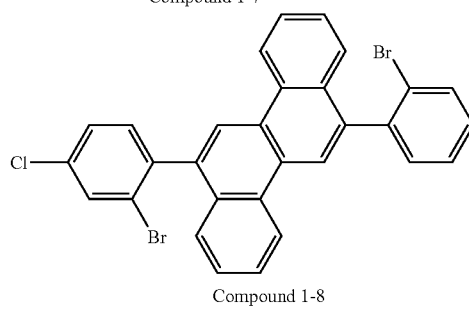

Compound 1-8

The following reagents and solvent were charged in a 300 ml-recovery flask, and stirred under a nitrogen flow at 80° C. for 4 hours.

Compound 1-6: 2.0 g (4.16 mmol)

Compound 1-7: 2.7 g (8.5 mmol)

Tetrakistriphenylphosphine palladium (0): 485 mg (0.42 mmol)

Toluene: 100 ml

Ethanol: 50 ml 2M-sodium carbonate aqueous solution: 20 ml

After completion of the reaction, toluene and water were added to separate the organic layer, dried over magnesium sulfate, and then the solvent was distilled off. Purification was carried out by silica gel column chromatography (developing solvent: toluene/heptane=1/9), and 1.81 g (yield 72%) of the compound 1-8 was obtained.

(3-3) Synthesis of Synthetic Intermediate Compound 1-9

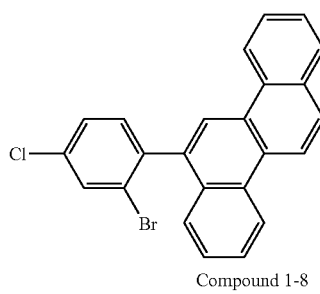

Compound 1-8

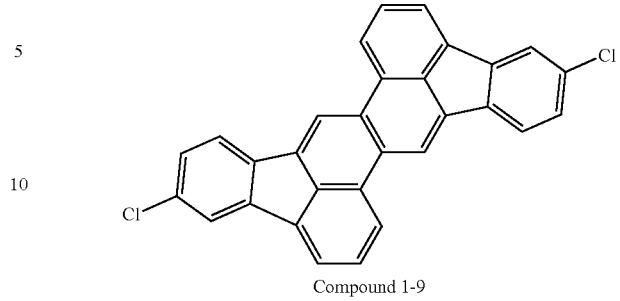

Compound 1-9

The following reagents and solvent were charged in a recovery flask, and stirred under a nitrogen flow at 100° C. for 8 hours.

Compound 1-8: 1.5 g (2.47 mmol)

LiCl: 636 mg (15.0 mmol)

1,8-diazabicyclo[5.4.0] 7-undecene: 943 mg (6.20 mmol)

Bistriphenylphosphine palladium (II) dichloride: 40 mg (0.24 mmol)

Dimethylformamide: 150 ml

After completion of the reaction, water was added thereto and stirred at room temperature for 1 hour. An orange precipitate was confirmed in the reaction solution and then filtered, and the filtrate was washed with water, methanol, and acetone. The filtrate was dried and 1.1 g (yield 51%) of the compound 1-9 was obtained.

With respect to the obtained compound, the molecular weight was measured.

(Molecular Weight)

It was confirmed that M+ was 445.3 by MALDI-TOF-MS (matrix-assisted laser deposition ionization—time of flight mass spectrometry), and the compound 1-9 was identified.

(3-4) Synthesis of Exemplified Compounds G-14 and G-19

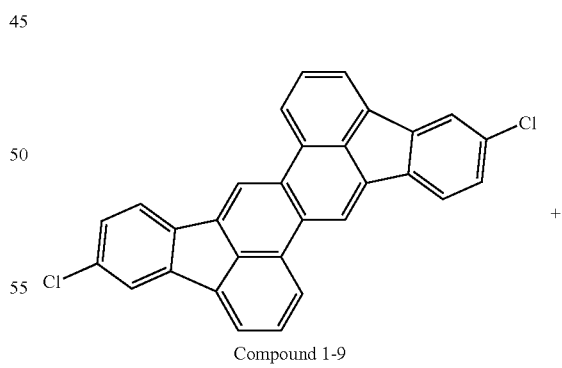

Compound 1-9

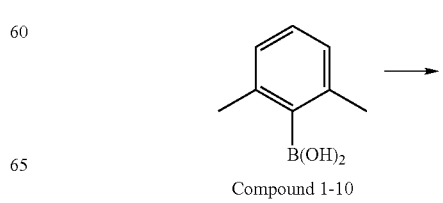

Compound 1-10

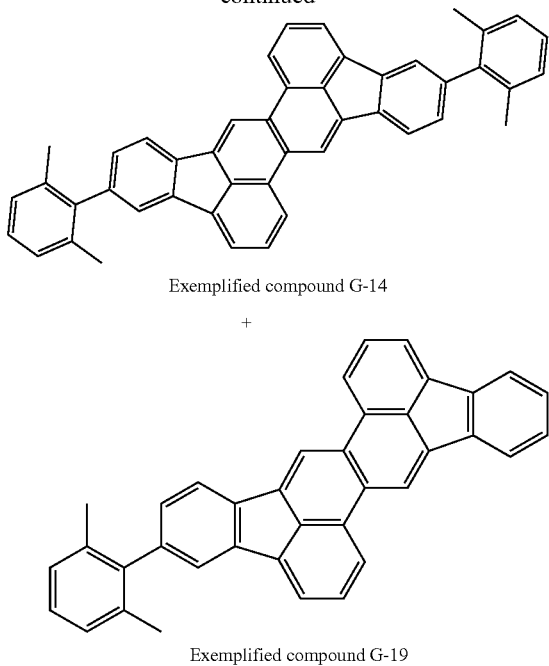

Exemplified compound G-14

+

Exemplified compound G-19

The following reagents and solvent were charged in a recovery flask, and stirred under a nitrogen flow at 80° C. for 8 hours.

Compound 1-9: 500 mg (1.12 mmol)
Compound 1-10: 100 mg (2.4 mmol)
Palladium (II) acetate: 75 mg (0.33 mmol)
2-dicyclohexylphosphino-2',6'-dimethoxybiphenyl: 410 mg (0.99 mmol)
Tripotassium phosphate: 713 mg (3.36 mmol)
Toluene: 50 ml After completion of the reaction, toluene and water were added to separate the organic layer, dried over magnesium sulfate, and then the solvent was distilled off. Purification was carried out by silica gel column chromatography (developing solvent: toluene/heptane=1/3), and 209 mg (yield 32%) of the exemplified compound G-14 and 97 mg (yield 18%) of the exemplified compound G-19 were obtained.

With respect to the obtained compound, the physical properties thereof were measured and evaluated.
(Molecular Weight)

It was confirmed that each M+ was 584.7 and 480.6 by MALDI-TOF-MS (matrix-assisted laser deposition ionization—time of flight mass spectrometry), and the exemplified compounds G-14 and G-19 were identified.
(NMR)

The structure of the exemplified compound G-14 was confirmed by NMR measurement.

$^1$H-NMR (CDCl$_3$, 400 MHz) σ (ppm) : 9.22 (s, 2H), 8.74 (d, 2H, J=9.6 Hz), 8.19 (d, 2H, J=9.2 Hz), 8.03 (d, 2H, J=8.2 Hz), 7.88 (dd, 2H, J=8.4 Hz, J=8.2 Hz), 7.78 (d, 2H, J=0.96 Hz), 7.27-7.20 (m, 8H), 2.18 (s, 12H)

The structure of the exemplified compound G-19 was also confirmed by NMR measurement.

$^1$H-NMR (CDCl$_3$, 400 MHz) σ (ppm) : 9.10 (s, 2H), 9.08 (s, 2H), 8.63 (d, 2H, J=9.6 Hz), 8.14 (d, 1H, J=7.2 Hz), 8.01-8.06 (m, 1H), 7.99 (dd, 1H, J=7.2 Hz, J=11.2 Hz), 7.95-7.92 (m, 1H), 7.84-7.76 (m, 2H), 7.46-7.42 (m, 2H), 7.26-7.18 (m, 4H), 2.19 (s, 6H)

(Light-Emitting Characteristics)

Measurement of light emission characteristics was performed in the same manner as in Example 1.

Absorption spectrum of a toluene solution (1×10$^{-5}$ mol/l) of the exemplified compounds G-14 and G-19 in a solution state was measured. After measuring the absorption spectrum, light emission spectrum (PL spectrum) of the toluene solution (1×10$^{-5}$ mol/l) of the exemplified compounds G-14 and G-19 was measured. Herein, as a result of the measurement of the absorption spectrum, an excitation wavelength was determined to be 340 nm. As a result of the measurement, PL spectrum shown in FIG. 7 was obtained. According to the PL spectrum shown in FIG. 7, the first peak and the second peak of the maximum light-emitting wavelength of the exemplified compound G-14 were respectively 444 nm and 470 nm, and found to show blue light emission, and the first peak and the second peak of the maximum light-emitting wavelength of the exemplified compound G-19 were respectively 440 nm and 467 nm, and found to show blue light emission.

Example 4

Synthesis of Exemplified Compound G-18

Exemplified compound G-18 was synthesized in the same synthesis method as Example 3. Specifically, the synthesis was carried out under the same conditions in Example 3 except for changing compound 1-10 to compound 1-11 in Example 1.

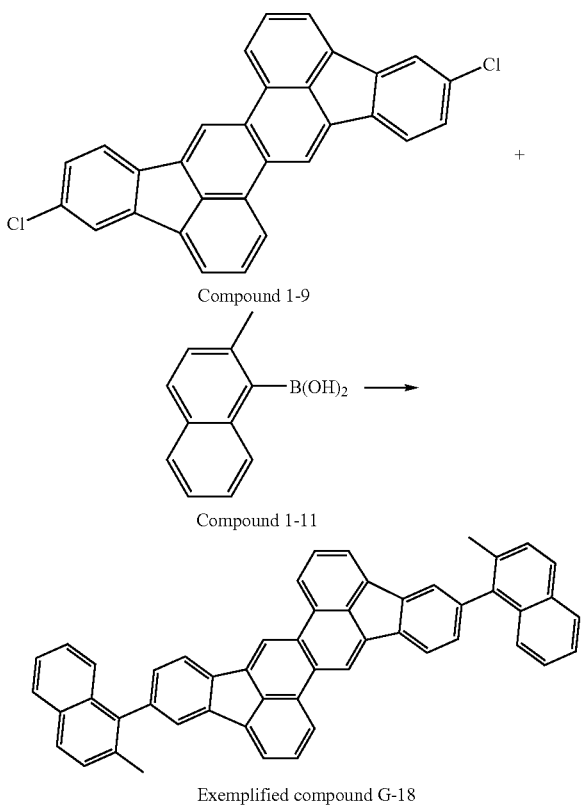

Compound 1-9

+

Compound 1-11

Exemplified compound G-18

With respect to the obtained compound, the physical properties thereof were measured and evaluated.
(Molecular Weight)

It was confirmed that M+ was 656.8 by MALDI-TOF-MS (matrix-assisted laser deposition ionization—time of flight mass spectrometry), and the exemplified compound G-18 was identified.

(NMR)

The structure of this compound was confirmed by NMR measurement.

$^1$H-NMR (CDCl$_3$, 60 MHz) σ (ppm) : 9.34 (s, 2H), 8.82 (d, 2H, J=5.8 Hz), 8.30 (d, 2H, J=6.3 Hz), 8.06 (d, 2H, J=5.8 Hz), 7.93-7.86 (m, 8H), 7.62 (d, 2H, J=7.1 Hz), 7.51 (d, 2H, J=7.1 Hz), 7.46-7.39 (m, 6H), 2.40 (s, 6H)

(Light-Emitting Characteristics)

Measurement of light emission characteristics was performed in the same manner as in Example 1.

Absorption spectrum of a toluene solution (1×10$^{-5}$ mol/l) of the exemplified compound G-18 in a solution state was measured. After measuring the absorption spectrum, a light emission spectrum (PL spectrum) of the toluene solution (1×10$^{-5}$ mol/l) of the exemplified compound G-18 was measured. Herein, as a result of the measurement of the absorption spectrum, an excitation wavelength was determined to be 355 nm. As a result of the measurement, PL spectrum shown in FIG. 7 was obtained. According to the PL spectrum shown in FIG. 7, the first peak and the second peak of the maximum light-emitting wavelength of the exemplified compound G-18 were respectively 442 nm and 469 nm, and found to show preferable blue light emission.

Example 5

Synthesis of Exemplified Compound G-22

(5-1) Synthesis of Synthetic Intermediate Compound 1-12

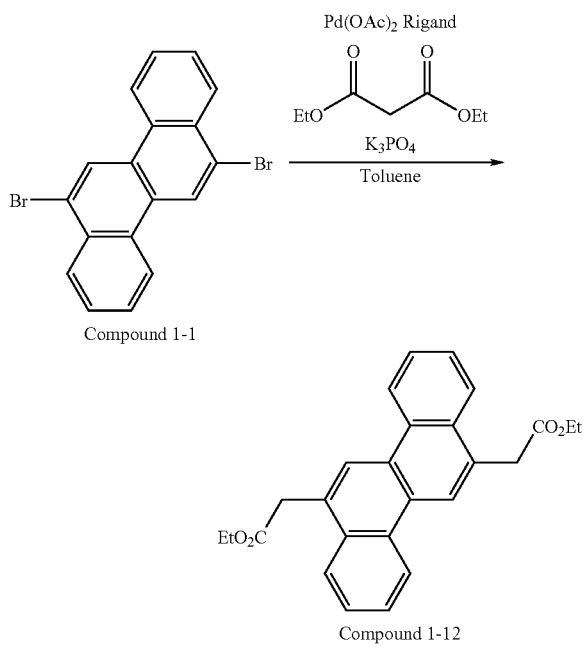

The following reagents and solvent were charged in a 300 ml-recovery flask, and stirred under a nitrogen flow at 80° C. for 18 hours.

Compound 1-1: 5.0 g (13.0 mmol)
Ethyl acetoacetate: 6.74 g (51.8 mmol)
Tripotassium phosphate: 16.5 g (77.7 mmol)
Palladium (II) acetate: 116 mg (0.52 mmol)
2-(ditertiary-butylphosphino)-2'-methoxybiphenyl: 324 mg (1.04 mmol)

Toluene: 100 ml
Ethanol: 15 ml

After completion of the reaction, toluene and water were added to separate the organic layer, dried over magnesium sulfate, and then the solvent was distilled off. Purification was carried out by silica gel column chromatography (developing solvent: toluene/chloroform=1/1), and 2.87 g (yield 55%) of the compound 1-12 was obtained.

(5-2) Synthesis of Synthetic Intermediate Compound 1-13

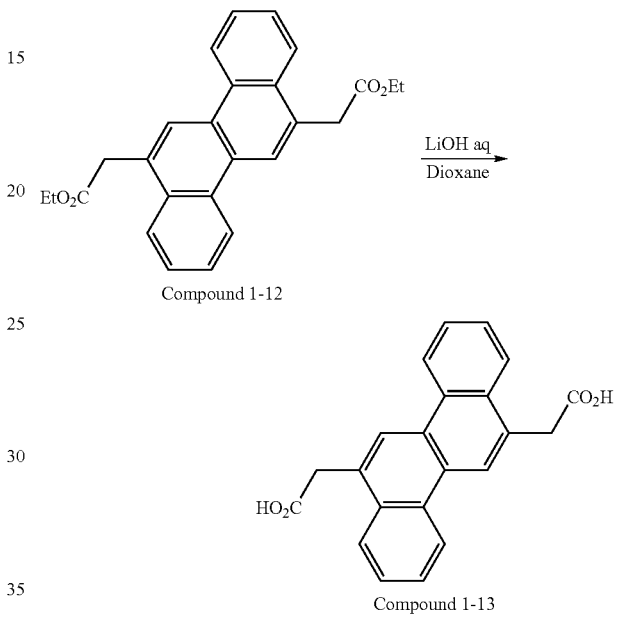

The following reagents and solvent were charged in a recovery flask, and stirred at 90° C. for 24 hours.

Compound 1-12: 3.76 g (89.6 mmol)
Dioxane: 30 ml
Lithium hydroxide monohydrate: 3.76 g (89.6 mmol)

Concentrated hydrochloric acid (20 ml) was gradually added to this suspension, and the mixture was stirred at room temperature for 5 hours. Then, water (200 ml) was added thereto and the precipitated crystal was separated by filtration. This crystal was sequentially washed with water, methanol, and diethyl ether and dried by high vacuum heating, and 2.87 g (yield 93%) of compound 1-13 was obtained.

(5-3) Synthesis of Synthetic Intermediate Compound 1-15

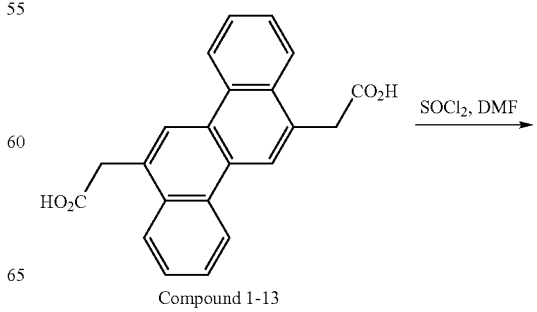

-continued

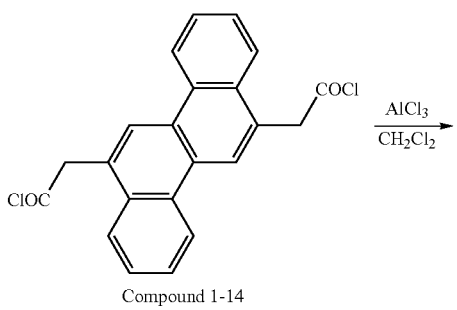
Compound 1-14

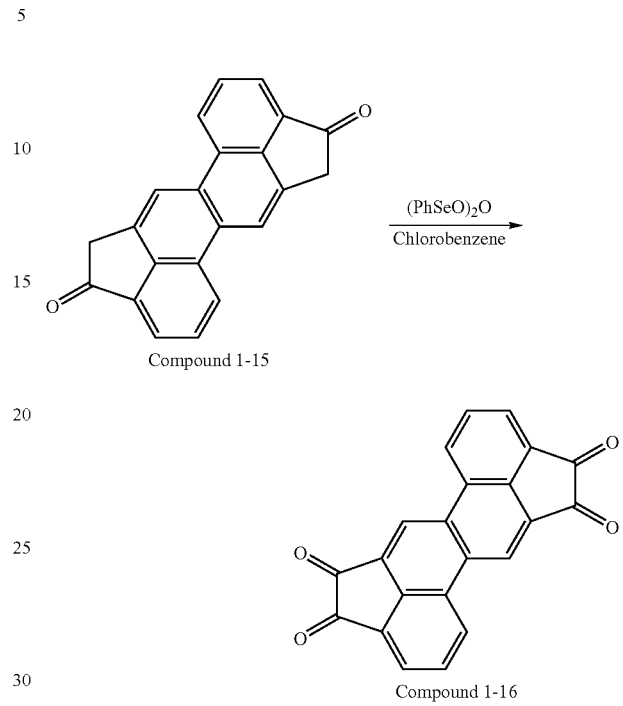
Compound 1-15

Compound 1-15

The following reagents and solvent were charged in a recovery flask, and stirred at 80° C. for 2 hours.
Compound 1-13: 2.87 g (6.36 mmol)
Thionyl chloride: 50 ml
Dimethylformamide: 300 μl This suspension was distilled off under reduced pressure, and the residual was sequentially added with dichloromethane (50 ml) and aluminum trichloride (2.1 g, 15.9 mmol), and the mixture was intensively stirred at room temperature for 18 hours. Concentrated hydrochloric acid (180 ml) was added to this suspension and stirred under heating for 1 hour. This suspension was separated by filtration, and this filtrate was subjected to Soxhlet extraction using chloroform as a solvent to concentrate the extracted substance. Purification was carried out by silica gel column chromatography (developing solvent: chloroform/ethyl acetate=15/1), and 1.2 g (yield 61%) of the compound 1-15 was obtained.

(5-4) Synthesis of Synthetic Intermediate Compound 1-16

Compound 1-16

The following reagents and solvent were charged in a recovery flask, and stirred at 130° C. for 18 hours.
Compound 1-15: 1.2 g (3.89 mmol)
Benzene selenic anhydride: 4.4 g (8.56 mmol)
Chlorobenzene: 60 ml This suspension was cooled to 100° C., and the precipitated crystal was separated by filtration. The obtained crystal was washed with hexane, and dried under high vacuum, and 1.27 g (yield 97%) of compound 1-16 was obtained.

(5-5) Synthesis of Synthetic Intermediate Compound 1-18

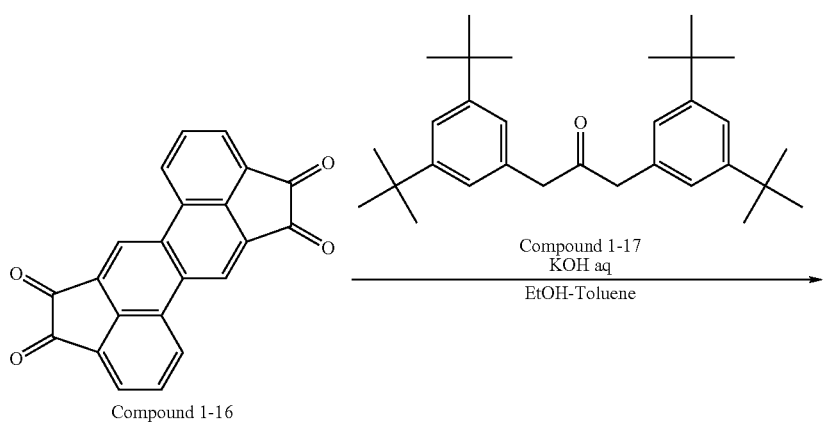
Compound 1-16

-continued

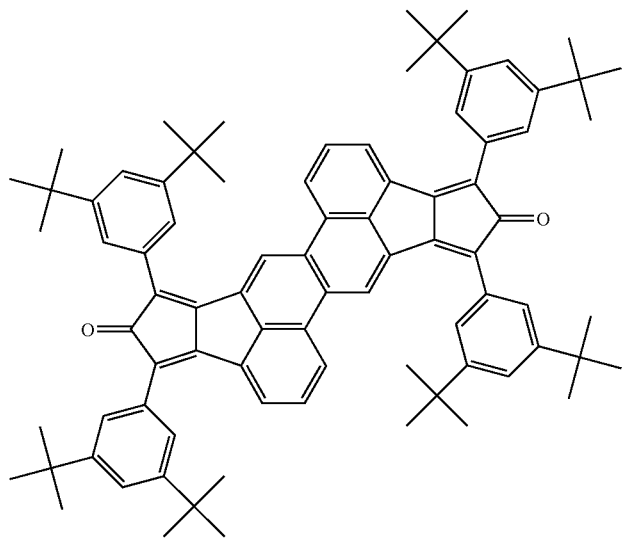

Compound 1-18

The following reagents and solvent were charged in a recovery flask, and stirred under a nitrogen flow at 80° C. for 18 hours.
Compound 1-16: 37 mg (0.0046 mmol)
Compound 1-17: 40 mg (0.0092 mmol)
Ethanol: 2 ml
Toluene: 0.4 ml
6N-potassium hydroxide: 300 μl After completion of the reaction, the crystal was left to be cooled to room temperature and separated by filtration. This crystal was sequentially washed with methanol and IPE and dried under high vacuum, and 55 mg (yield 99%) of compound 1-18 was obtained.

(5-6) Synthesis of Exemplified Compound G-22

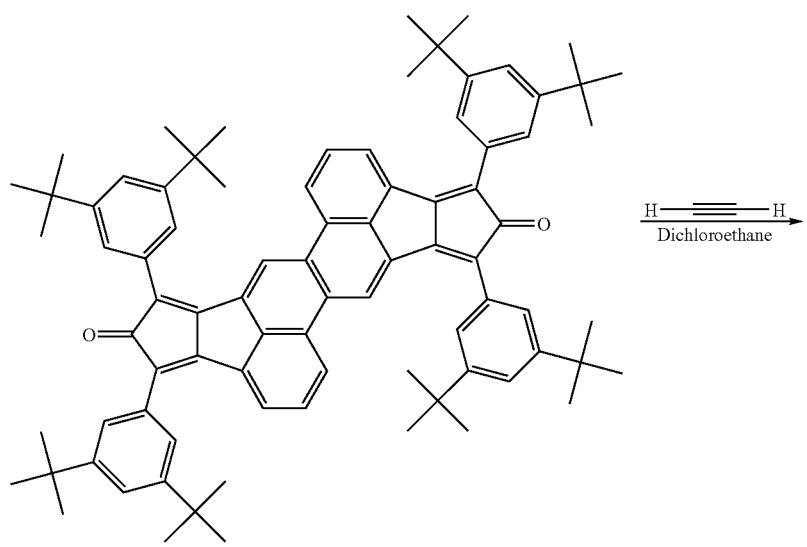

Compound 1-18

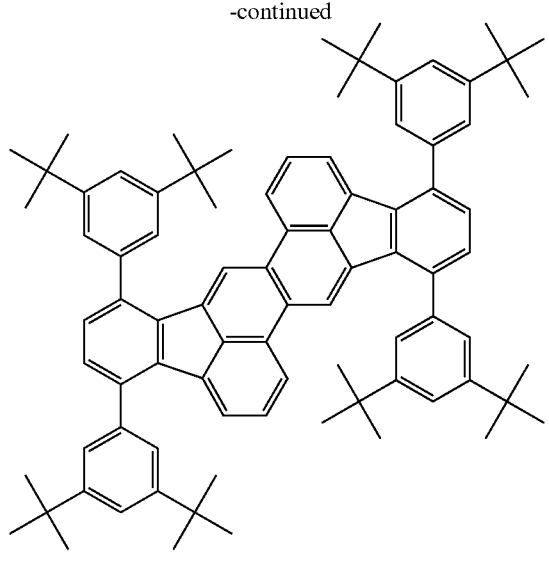

Exemplified compound G-22

The following reagent, solvent, and acetylene gas were charged in an autoclave and sealed, and stirred at 190° C. for 24 hours.

Compound 1-18: 200 mg (0.176 mmol)
Dichloroethane: 4 ml

After completion of the reaction, the crystal was left to be cooled to room temperature and separated by filtration. This crystal was sufficiently washed with hexane/toluene=2/1. Purification was carried out by silica gel column chromatography (developing solvent: hexane/chloroform=4/1), and 0.14 g (yield 70%) of the exemplified compound G-22 was obtained.

With respect to the obtained compound, the physical properties thereof were measured and evaluated.
(Molecular Weight)

It was confirmed that M+ was 1129.68 by MALDI-TOF-MS (matrix-assisted laser deposition ionization—time of flight mass spectrometry), and the exemplified compound G-22 was identified.
(NMR)

The structure of this exemplified compound G-22 was confirmed by NMR measurement.

$^1$H-NMR (CDCl$_3$, 400 MHz) σ (ppm): 8.01 (s, 2H), 7.80 (d, 2H, J=8.0 Hz), 7.80 (t, 2H, J=2.0 Hz), 7.57 (t, 2H, J=2.0 Hz), 8.18-8.16 (m, 2H), 8.07 (t, 2H, J=2.0 Hz), 7.54 (d, 4H, J=2.0 Hz), 7.53 (d, 4H, J=2.0 Hz), 7.40-7.32 (m, 4H), 1.42 (s, 36H), 1.40 (s, 36H)
(Light-Emitting Characteristics)

Measurement of light emission characteristics was performed in the same manner as in Example 1.

Figure 11:
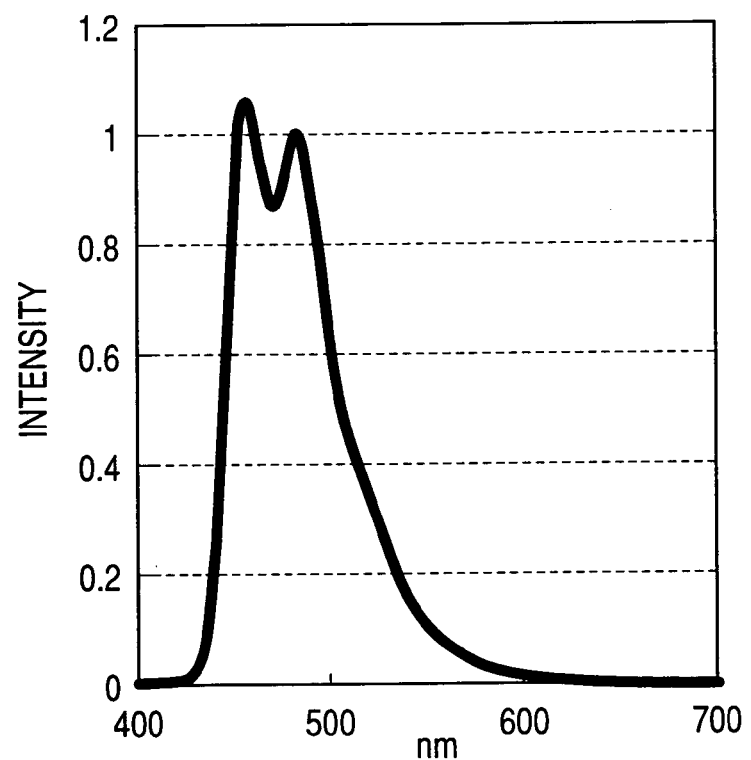
FIG. 11 is a view illustrating a PL spectrum (excitation wavelength: 355 nm) of a toluene solution ($1\times10^{-5}$ mol/l) of an exemplified compound G-22.

Absorption spectrum of a toluene solution (1×10$^{-5}$ mol/l) of the exemplified compound G-22 in a solution state was measured. After measuring the absorption spectrum, a light emission spectrum (PL spectrum) of the toluene solution (1×10$^{-5}$ mol/l) of the exemplified compound G-22 was measured. Herein, as a result of the measurement of the absorption spectrum, an excitation wavelength was determined to be 355 nm. As a result of the measurement, PL spectrum shown in FIG. 11 was obtained. According to the PL spectrum shown in FIG. 11, the first peak and the second peak of the maximum light-emitting wavelength of the exemplified compound G-22 were respectively 458 nm and 486 nm, and found to show preferable blue light emission.

Example 6

Synthesis of Exemplified Compound G-24

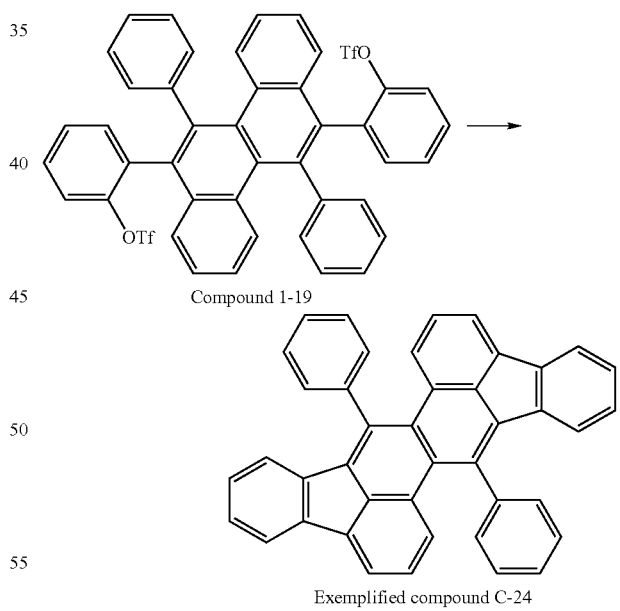

Compound 1-19

Exemplified compound C-24

The following reagents and solvent were charged in a recovery flask, and stirred under a nitrogen atmosphere at 150° C. for 1 hour.

Compound 1-19: 500 mg (0.603 mmol)
LiCl: 76 mg (1.81 mmol)
1,8-diazabicyclo[5.4.0] 7-undecene: 918 mg (6.03 mmol)
Palladium acetate: 13.5 mg (0.0603 mmol)
2-dicyclohexylphosphino-2',6'-dimethoxybiphenyl: 56.8 mg (0.133 mmol)

Dimethylformamide: 30 ml

After completion of the reaction, ethyl acetate and water were added to separate the organic layer, dried over magnesium sulfate, and then the solvent was distilled off. Purification was carried out by silica gel column chromatography (developing solvent: toluene/heptane=1/2), and 32 mg (yield 10%) of the exemplified compound G-24 was obtained.

With respect to the obtained compound, the physical properties thereof were measured and evaluated.

(Molecular Weight)

It was confirmed that M+was 528.6 by MALDI-TOF-MS (matrix-assisted laser deposition ionization—time of flight mass spectrometry), and the exemplified compound G-24 was identified.

Example 7

Synthesis of Exemplified Compound G-20

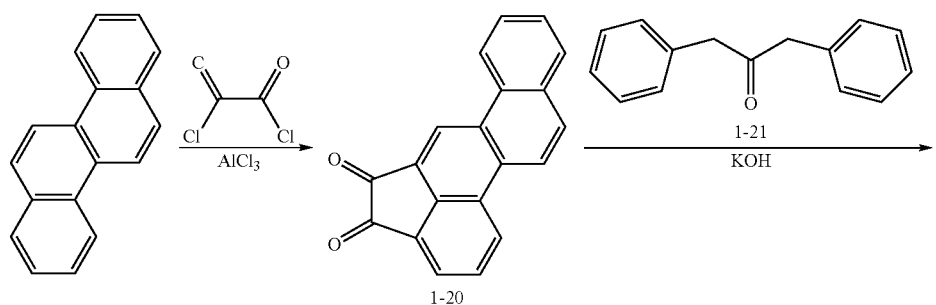

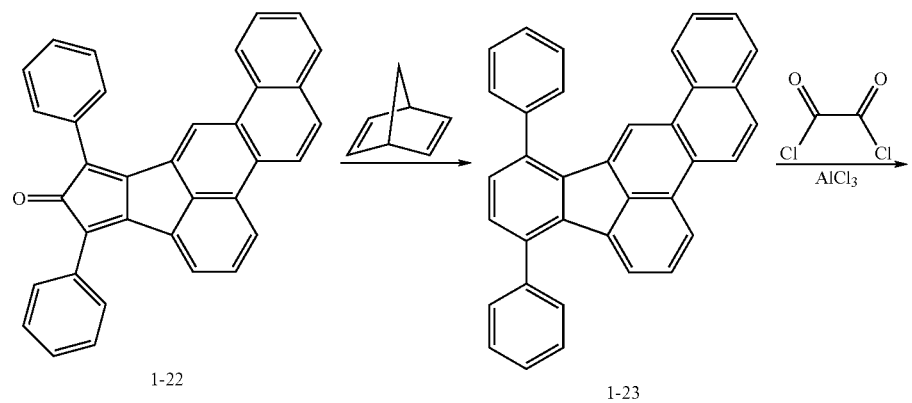

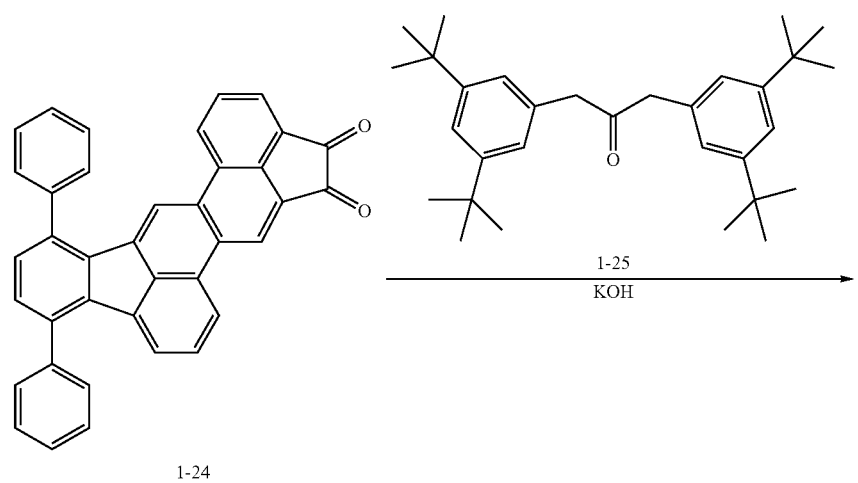

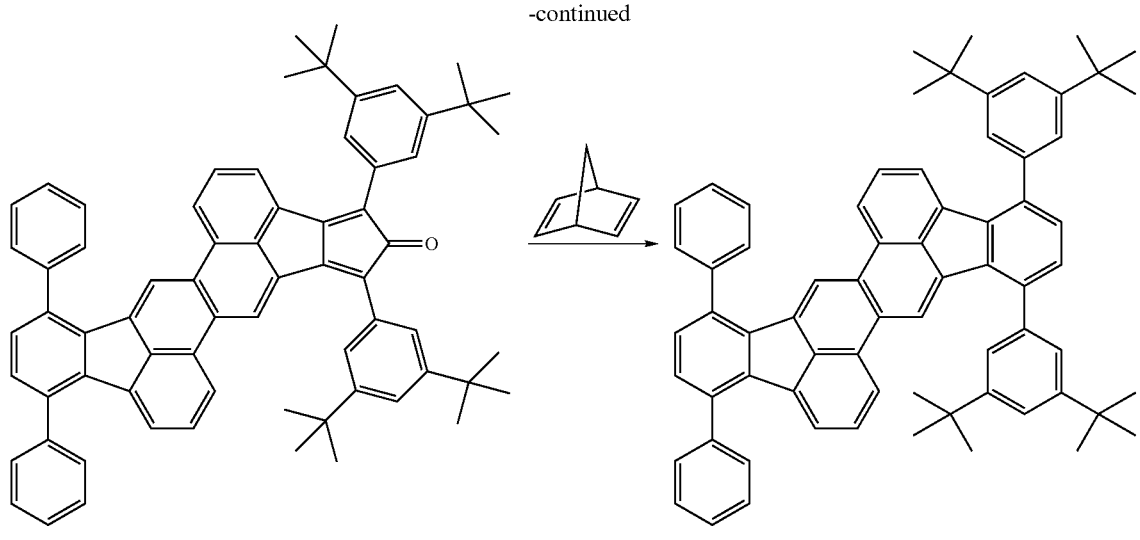

1-26　　　　　　　　　　　　　　　　　　　　G-20

(7-1) Synthesis of Compound 1-20

20.0 g (87.6 mmol) of chrysene, 46.7 g (350 mmol) of aluminum chloride, and 400 ml of dichloromethane were charged in 500 ml three-necked flask, and 55.6 g (438 mmol) of oxalyl chloride was dropped under nitrogen atmosphere at temperature of −78 ° C. while stirring, and then the mixture was further stirred for 30 minutes, and the reaction temperature was risen to the room temperature over 2 hours. The reaction mixture was poured into 4 L of ice water with stirring, and generated solid was filtrated out and the solid was dispersed and washed with 100 ml of methanol. The solid was filtrated and dried under vaccum heating to obtain 21.5 g (yield: 87%) of compound 1-20 (orange powder).

(7-2) Synthesis of Compound 1-22

2.01 g (7.10 mmol) of compound 1-20, 1.50 g (7.13 mmol) of compound 1-21 and 100 ml of ethanol were charged in 200 ml three-necked flask, and 25 ml of water solution dissolved 4.00 g of potassium hydroxide was dropped under nitrogen atmosphere at room temperature with stirring. Then the mixture was heated to 75° C. and stirred for one hour 30 minutes. The reaction liquid was cooled and precipitated solid was filtrated and dried to obtain 3.08 g (yield: 95%) of compound 1-22 (green powder).

(7-3) Synthesis of Compound 1-23

3.00 g (6.58 mmol) of compound 1-22, 4.97 g (54 mmol) of 2,5-norbornadiene, and 40 ml of acetic anhydride were charged in 200 ml three-necked flask, and the mixture was heated to 90° C. under nitrogen atmosphere, and stirred for 18 hours. The reaction mixture was cooled to room temperature and the solvent was distilled off under reduced pressure, and then the residue was purified by silica gel chromatography (development solvent: mixture of toluene and heptane) to obtain 1.58 g (yield: 53%) of compound 1-23 (yellow powder).

(7-4) Synthesis of Compound 1-24

1.00 g (2.20 mmol) of compound 1-23, 1.06 g (7.92 mmol) of aluminum chloride, and 50 ml of dichloromethane were charged in 100 ml three-necked flask, and 1.11 g (8.80 mmol) of oxalyl chloride was dropped under nitrogen atmosphere at temperature of −78° C. while stirring, and then the mixture was further stirred for 30 minutes, and the reaction temperature was risen to the room temperature over 2 hours. The reaction mixture was poured into 1 L of ice water with stirring, and generated solid was filtrated out and the solid was dispersed and washed with 30 ml of methanol. The solid was filtrated and dried under vaccum heating to obtain 0.894 g (yield: 80%) of compound 1-24 (orange powder).

(7-5) Synthesis of Compound 1-26

0.890 g (1.75 mmol) of compound 1-24, 0.855 g (1.97 mmol) of compound 1-25, 100 ml of ethanol, and 10 ml of toluene were charged in 200 ml three-necked flask, and 5 ml of water solution dissolved 1.11 g of potassium hydroxide was dropped under nitrogen atmosphere at room temperature with stirring. Then the mixture was heated to 75° C. and stirred for two hours 30 minutes. The reaction liquid was cooled and precipitated solid was filtrated and dried to obtain 0.49 g (yield: 31%) of compound 1-26 (green powder).

(7-6) Synthesis of Exemplified Compound G-20

0.49 g (0.541 mmol) of compound 1-26, 4.97 g (54 mmol) of 2,5-norbornadiene, and 40 ml of acetic anhydride were charged in 200 ml three-necked flask, and the mixture was heated to 90° C. under nitrogen atmosphere, and stirred for 18 hours. The reaction mixture was cooled to room temperature and the solvent was distilled off under reduced pressure, and then the residue was purified by silica gel chromatography (development solvent: mixture of toluene and heptane) to obtain 0.17 g (yield: 35%) of exemplified compound G-20 (yellow powder).

With respect to the obtained compound, the physical properties thereof were measured and evaluated.

(Molecular Weight)

It was confirmed that M+was 905.5 by MALDI-TOF-MS (matrix-assisted laser deposition ionization—time of flight mass spectrometry), and the exemplified compound G-20 was identified.

(NMR)

The structure of this exemplified compound G-20 was confirmed by NMR measurement.

1H-NMR (CDCl$_3$, 400 MHz) σ (ppm): 8.35 (s, 1H), 8.00 (s, 1H), 7.81 (dd, 2H, J=8.4 Hz, J=10.4 Hz), 7.76-7.73 (m, 3H), 7.69-7.64 (m, 5H), 7.56-7.50 (m, 8H), 7.45-7.30 (m, 7H), 7.22 (d, 1H, J=7.2 Hz), 1.42 (s, 18H), 1.40 (s, 18H)

(Light-Emitting Characteristics)

Measurement of light emission characteristics was performed in the same manner as in Example 1.

Figure 12:
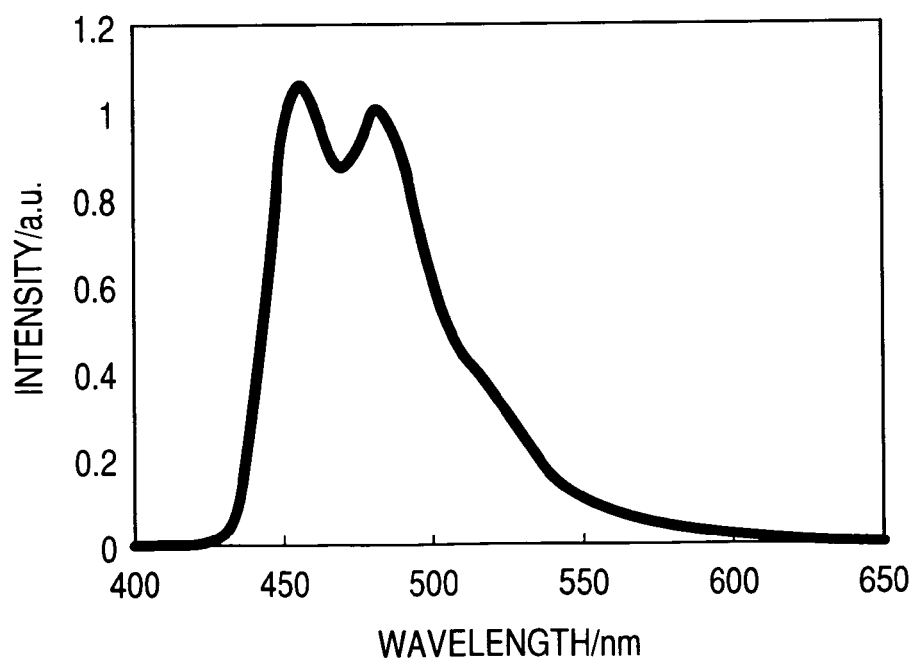
FIG. 12 is a view illustrating a PL spectrum (excitation wavelength: 355 nm) of a toluene solution ($1\times10^{-5}$ mol/l) of an exemplified compound G-20.

Absorption spectrum of a toluene solution ($1 \times 10^{-5}$ mol/l) of the exemplified compound G-20 in a solution state was measured. After measuring the absorption spectrum, a light emission spectrum (PL spectrum) of the toluene solution ($1 \times 10^{-5}$ mol/l) of the exemplified compound G-20 was measured. Herein, as a result of the measurement of the absorption spectrum, an excitation wavelength was determined to be 355 nm. As a result of the measurement, PL spectrum shown in FIG. 12 was obtained. According to the PL spectrum shown in FIG. 12, the first peak and the second peak of the maximum light-emitting wavelength of the exemplified compound G-20 were respectively 456 nm and 482 nm, and found to show preferable blue light emission.

Exemplified compounds B-2, C-12, D-1, E-8, F-6, G-1, G-2, G-7, G-10, G-40, G-41 and H-2 can be synthesized under the same conditions in Example 1, except for using the compounds shown in Tables 1 and 2 shown below in place of the compounds 1-1 and 1-2 in Example 1.

TABLE 1

| Exemplified compounds | Dibromochrysene derivative | 2-hydroxyphenylboronic acid derivative |
|---|---|---|
| B-2 | | |
| C-12 | | |
| D-1 | | |
| E-8 | | |

TABLE 1-continued
| Exemplified compounds | Dibromochrysene derivative | 2-hydroxyphenylboronic acid derivative |
|---|---|---|
| F-6 | 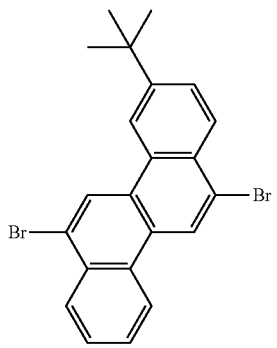 | 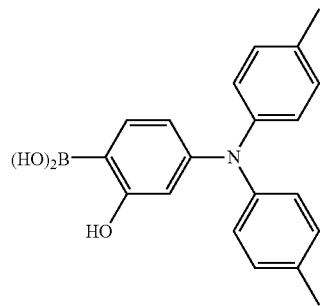 |
| G-1 | 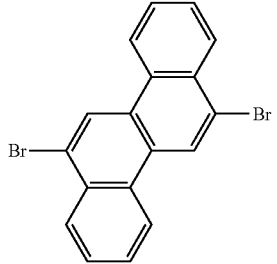 | 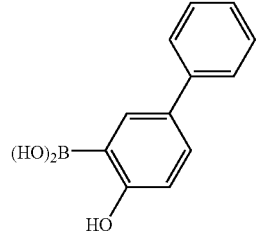 |
| G-2 | 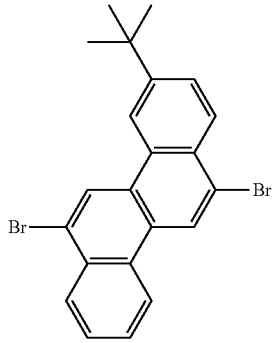 | 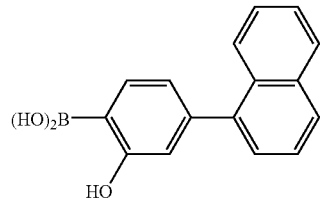 |
TABLE 2
| Exemplified compounds | Dibromochrysene derivative | 2-hydroxyphenylboronic acid derivative |
|---|---|---|
| G-7 | 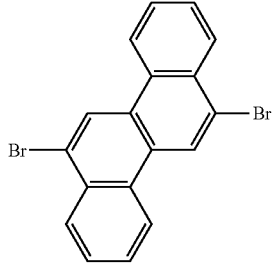 | 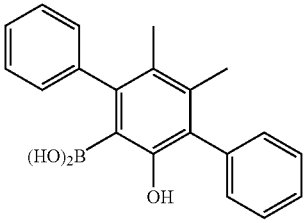 |

TABLE 2-continued

| Exemplified compounds | Dibromochrysene derivative | 2-hydroxyphenylboronic acid derivative |
|---|---|---|
| G-10 | | |
| G-40 | | |
| G-41 | | |
| H-2 | | |

Example 8

Production of Organic Light-Emitting Service

In the present Example, an organic light-emitting device shown in FIG. 3 was produced. First, indium tin oxide (ITO) (anode 2) was patterned on a glass substrate (substrate 1) with a film thickness of 100 nm so as to prepare an ITO electrode-attached glass plate. Then, on this ITO electrode-attached glass plate, a layer made of an organic compound and a cathode were continuously formed into a film by vacuum deposition due to resistance heating. Specifically, first, a compound 2 shown in the following was formed into a film having a thickness of 20 nm as a hole transporting layer 5. Then, as a light-emitting layer 3, a compound 3 shown in the following to be a host and the exemplified compound A-1 to be a guest were co-deposited so that a content of the exemplified compound A-1 was 1% by weight based on the compound 3. Herein, the film thickness of the light-emitting layer 3 was set at 30 nm. Then, as an electron transporting layer, a compound 4 shown in the following was formed into a film with a thickness of 30 nm. KF was then formed into a film with a thickness of 1 nm, and finally, Al was formed into a film with a thickness of 100 nm. Herein, KF and Al function as cathode 4.

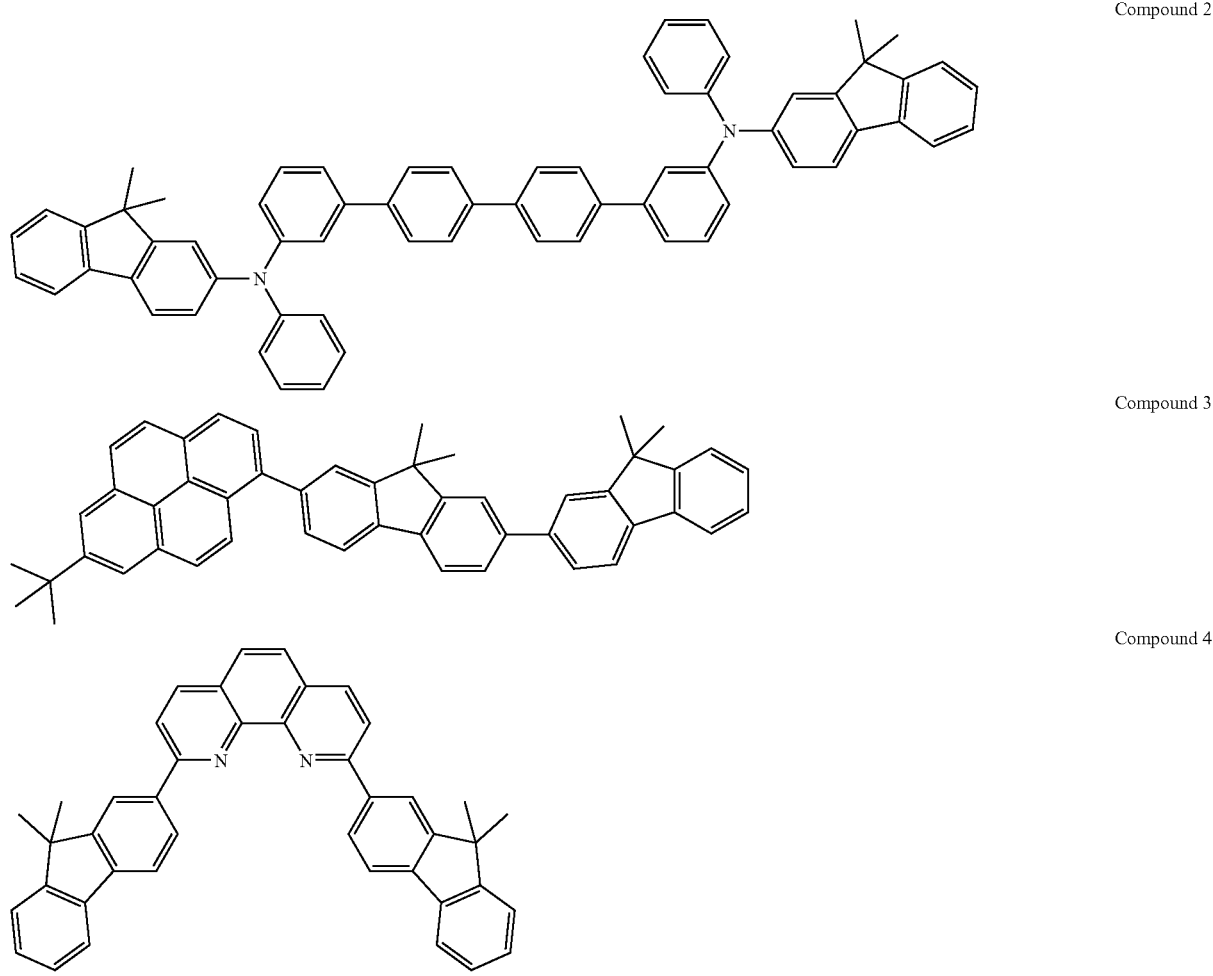

Compound 2

Compound 3

Compound 4

In addition, when forming a film, a pressure in a vacuum chamber was set at 10⁻⁵ Pa. Further, for producing a device, a facing electrode area was set at 3 mm². The organic light-emitting device was thus obtained as described above.

The obtained organic light-emitting device was evaluated by measuring the properties thereof. Specifically, current-voltage characteristics of the device was measured by a minute amperemeter 4140B manufactured by Hewlett-Packard Co., and a light luminescence of the device was measured by BM7 manufactured by Topcon Corporation. As a result, blue light emission having a light luminescence of 360 cd/m² was observed at an applied voltage of 4.0 V. When the device was driven under the conditions such that a current density was kept at 30 mA/cm² under a nitrogen atmosphere and a voltage was applied for 100 hours, an initial luminescence was 800 cd/m² to 740 cd/m². According to the above description, it can be recognized that the organic light-emitting device having favorable light-emitting efficiency and excellent durability was realized.

Example 9

Production of Organic Light-Emitting Device

Evaluation of a device of the exemplified compound C-6 was performed in the same production method of the device as Example 8. Specifically, the device was produced under the same conditions as in Example 8, except for changing the exemplified compound A-1 into the exemplified compound C-6 in Example 8.

As a result, blue light emission having a light luminescence of 810 cd/m² was observed at an applied voltage of 4.0 V. When the device was driven under the conditions such that a current density was kept at 30 mA/cm² under a nitrogen atmosphere and a voltage was applied for 100 hours, an initial luminescence was 1250 cd/m² to 1000 cd/m². According to the above description, it can be recognized that the organic light-emitting device having favorable light-emitting efficiency and excellent durability was realized.

Example 10

Production of Organic Light-Emitting Device

Evaluation of a device of the exemplified compound G-14 was performed in the same production method of the device as Example 8. Specifically, the device was produced under the same conditions as in Example 8, except for changing the exemplified compound A-1 into the exemplified compound G-14 in Example 8.

As a result, blue light emission having a light luminescence of 950 cd/m² was observed at an applied voltage of 4.0 V.

When the device was driven under the conditions such that a current density was kept at 30 mA/cm² under a nitrogen atmosphere and a voltage was applied for 100 hours, an initial luminescence was 1320 cd/m² to 1210 cd/m². According to the above description, it can be recognized that the organic light-emitting device having favorable light-emitting efficiency and excellent durability was realized.

Example 11

Production of Organic Light-Emitting Device

Evaluation of a device of the exemplified compound G-18 was performed in the same production method of the device as Example 8. Specifically, the device was produced under the same conditions as in Example 8, except for changing the exemplified compound A-1 into the exemplified compound G-18 in Example 8.

As a result, blue light emission having a light luminescence of 1250 cd/m² was observed at an applied voltage of 4.0 V. When the device was driven under the conditions such that a current density was kept at 30 mA/cm² under a nitrogen atmosphere and a voltage was applied for 100 hours, an initial luminescence was 1500 cd/m² to 1400 cd/m². According to the above description, it can be recognized that the organic light-emitting device having favorable light-emitting efficiency and excellent durability was realized.

Example 12

Production of Organic Light-Emitting Device

Evaluation of a device of the exemplified compound G-20 was performed in the same production method of the device as Example 8. Specifically, the device was produced under the same conditions as in Example 8, except for changing the exemplified compound A-1 into the exemplified compound G-20 in Example 8.

As a result, blue light emission having a light luminescence of 1340 cd/m² was observed at an applied voltage of 4.0 V. When the device was driven under the conditions such that a current density was kept at 30 mA/cm² under a nitrogen atmosphere and a voltage was applied for 100 hours, an initial luminescence was 1480 cd/m² to 1320 cd/m². According to the above description, it can be recognized that the organic light-emitting device having favorable light-emitting efficiency and excellent durability was realized.

This application claims the benefit of Japanese Patent Application No. 2007-096343, filed Apr. 2, 2007, and No. 2008-038299, filed Feb. 20, 2008 which are hereby incorporated by reference herein in their entirety.

The invention claimed is:

1. A condensed ring aromatic compound for an organic light-emitting device represented by the following general formula [1]:

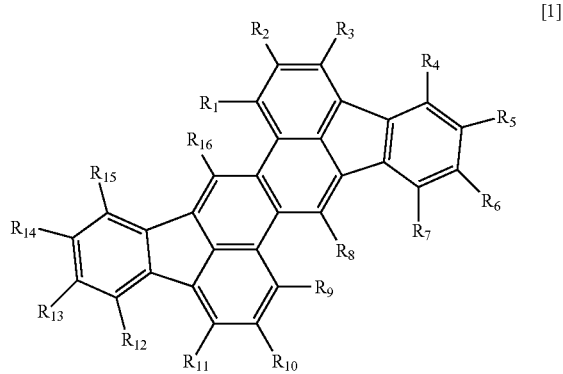

wherein $R_1$ to $R_{16}$ each independently represent a hydrogen atom, a halogen atom, a substituted or unsubstituted alkyl group, a substituted or unsubstituted alkoxy group, a substituted or unsubstituted aryloxy group, a substituted or unsubstituted amino group, a substituted or unsubstituted aryl group, or a substituted or unsubstituted heterocyclic group, and may be the same or different.

2. An organic light-emitting device comprising an anode and a cathode, and a layer made of an organic compound interposed between the anode and the cathode, wherein the layer made of an organic compound contains the condensed ring aromatic compound according to claim 1.

3. The organic light-emitting device according to claim 2, wherein the layer made of an organic compound which contains the condensed ring aromatic compound is a light-emitting layer.

* * * * *